United States Patent
Stenos et al.

(10) Patent No.: US 12,364,220 B2
(45) Date of Patent: Jul. 22, 2025

(54) SUSTAINABLY BOOSTING CARBON DIOXIDE FIXATION FOR GROWING MICRO-ALGAE

(71) Applicant: Solmeyea Monoprosopi I.K.E., Attica (GR)

(72) Inventors: Vasilis Stenos, Athens (GR); Hariklia Gavala, Copenhagen (DK); Ioannis Skiadas, Copenhagen (DK); Diego Grumbach, Asnieres-sur-Seine (FR)

(73) Assignee: Solmeyea Monoprosopi I.K.E., Attica (GR)

( * ) Notice: Subject to any disclaimer, the term of this patent is extended or adjusted under 35 U.S.C. 154(b) by 489 days.

(21) Appl. No.: 17/962,024

(22) Filed: Oct. 7, 2022

(65) Prior Publication Data

US 2023/0110971 A1  Apr. 13, 2023

Related U.S. Application Data

(60) Provisional application No. 63/253,306, filed on Oct. 7, 2021.

(51) Int. Cl.
| | | |
|---|---|---|
| A01G 33/00 | (2006.01) | |
| A01G 7/02 | (2006.01) | |
| C12M 1/00 | (2006.01) | |
| C12M 1/12 | (2006.01) | |

(52) U.S. Cl.
CPC ............ *A01G 33/00* (2013.01); *A01G 7/02* (2013.01); *C12M 21/02* (2013.01); *C12M 25/18* (2013.01); *C12M 43/04* (2013.01)

(58) Field of Classification Search
CPC ..................................................... A01G 33/00
See application file for complete search history.

(56) References Cited

FOREIGN PATENT DOCUMENTS

WO   WO-2010150190 A2 * 12/2010 ............ C12M 21/02

* cited by examiner

*Primary Examiner* — Albert M Navarro
(74) *Attorney, Agent, or Firm* — DP IP GROUP; Franco De Liguori

(57) ABSTRACT

A system, comprising a Trickle Bed Reactor (TBR), a microalgae cultivation module, and a feedback module is used to sustainably boost CO2 fixation for growing microalgae. The TBR comprises a packing material in the form of non-porous particles with a high surface-to-volume ratio, forming a substrate for attachment of Volatile Fatty Acid (VFA) producing microbes, fed with CO2 (and/or CO), H2, nutrients, and a moistening liquid. The TBR output is fed to the microalgae cultivation module which uses micro-algae selected or adapted for increased productivity in the presence of VFAs. No CO2 needs to be fed to the microalgae cultivation module. At least part of the output of the microalgae cultivation module is fed by the feedback module back to the TBR either as a source of nutrients or for as a means backflushing for unclogging or expulsing the packing material from the TBR for cleaning/disinfection. The overall CO2 balance of the system operation is negative.

12 Claims, 9 Drawing Sheets

SUSTAINABLY BOOSTING CARBON DIOXIDE FIXATION FOR GROWING MICRO-ALGAE

RELATED APPLICATION

This application claims the benefit of U.S. Provisional Patent Application No. 63/253,306, filed on Oct. 7, 2021.

BACKGROUND

Field

The present invention relates to a system and method for sustainably boosting $CO_2$ fixation for growing micro-algae.

Background

Environmental concerns relating to global warming by greenhouse gases and financial concerns relating to the costs of fixating Carbon Dioxide ($CO_2$) and buying pollution rights (in the European Union (EU) and other countries) have enhanced research in $CO_2$ fixation. In particular, $CO_2$ fixation technologies have been developed for converting $CO_2$ into useful products, like chemicals, fuels, food supplements, etc.

$CO_2$ (and other gases like CO) are present in the atmosphere. Although theoretically possible to capture $CO_2$ from the atmosphere, its low concentration (409.8 parts per million (ppm for short, with a range of uncertainty of plus or minus 0.1 ppm) in the air makes it very difficult and expensive. As a result, $CO_2$ is more efficiently sourced from the main sources, i.e. $CO_2$ producers.

$CO_2$ and (other gases like CO) are produced in large volumes as part of burning or gasification processes. Burning of fossil fuels is the primary creator of $CO_2$ (apart from volcanic eruptions), which is released in the atmosphere and is the main greenhouse gas (though less harming than methane, which currently exists in relatively small quantities). Burning processes are thermochemical processes which produce off-gases, which contain $CO_2$. Among the main producers of off-gasses are heavy industries like cement factories, power plants and internal combustion engines. Although $CO_2$ capture from off-gasses is proposed in the art, it is still an expensive process as, again, the $CO_2$ concentration in off-gasses is not very high (respective concentration ranges of 0.15-0.45 mole $CO_2$ per mole MEA and 200-800 ppm for both $H_2SO_3$ and $HNO_3$) though higher than in atmosphere. As in atmosphere, off-gasses contain a large number of other gasses, and typically also contain other pollutants like dust, ashes, tar, etc., which further complicate $CO_2$ capture from off-gasses and make it less efficient and more expensive.

Gasification is the complete thermal breakdown of solid carbonaceous feedstock into a combustible mixture of gasses (usually known as synthesis gas or syngas and consisting mainly of CO, $H_2$ and $CO_2$. Gasification takes place in an enclosed reactor (gasifier) in the presence of an oxidizing agent (e.g. air, $O_2$, $H_2O$ etc.), which is supplied externally at a ratio lower than it is required for the complete oxidation of the feedstock.

Syngas can directly be used for the generation of heat and power. However, it can also serve as feedstock for production of liquid fuels, chemicals and materials. Because of this flexibility of application, gasification has been proposed as the basis for refineries that would provide a variety of energy and chemical products, including electricity and transportation fuels. Raw materials for gasification may be of fossil origin (e.g. coal), however, the focus should be on sustainable options such as biomass and wastes. Biomass such as lignocellulosic energy crops are potential candidates for gasification. Nonetheless, the increase in arable land required for farming of these feedstocks has indirect implications on land use and food prices (see "food vs fuel" debate), bringing about a ripple effect with negative environmental and socio-economic impacts in many regions of the world. As a result, alternative sources of 2nd generation biomasses are preferable. Such sources are lignocellulosic biomass waste like residues from the forestry, agricultural and food sector, which come with very similar characteristics with the above-mentioned woody biomasses but also some additional challenging carbonaceous material such as sewage sludge, municipal solid wastes or waste plastics that also come with disposal problems. As previously presented for off-gas, syngas poses similar challenges to $CO_2$ capture due to its constituent gasses and other pollutants (e.g. tar, ash, dust), and as a result reduced efficiency, which leads to higher costs is encountered.

In order to remove gas from off-gas and syngas, a process more correctly referred to $CO_2$ fixation, which fixates $CO_2$ into other products, useful as intermediate or final products for other processes or for sale and commercial exploitation.

The prime $CO_2$ fixation technologies employ catalysts, electrochemical processes, or biological processes using micro-organisms. The use of microorganisms for $CO_2$ fixation (e.g. into acids) is becoming widely adopted in industry and the research community. Typically, $CO_2$, Carbon Monoxide (CO), nutrients, and Hydrogen ($H_2$) are inputted into a Trickle Bed Reactor (TBR) where selected and/or modified microbes convert the gas inputs into methane, fatty acids, and/or other products.

A TBR is a solid-liquid-gas contacting device, usually in the form of a tube, or tubes connected in parallel and oriented vertically or inclined, wherein a liquid stream flows downward over a bed of catalyst (e.g. in the form of beads, granules, pellets, etc.) with pressure difference serving as the driving force for the liquid to trickle onto the catalyst and form fine films, rivulets or droplets. The gas stream can either flow concurrent with the liquid or countercurrent to it through the bed. TBRs are primarily operated in continuous mode but are sometimes used in semi-batch processes.

TBRs may be run in stable-continuous, pulsing, spray, or bubble flow regimes depending on the application.

TBR are very well known and widely used in the field of chemical catalysis and environmental biotechnology (wastewater, liquid and gas effluent treatment for reducing the concentration of polluting components) and at a much lesser extent in Industrial Biotechnological applications. Their efficiency in biological applications depends on several parameters, including the choice of microbes, the liquid and nutrients fed on the microbes, the operating temperature, pH, and flow. Other influencing factors are pollutants, gas mixtures, purity of the microbes, etc. As skilled persons know, the control of all these parameters for increasing the efficiency of TBRs is not an easy task, especially taking into account that off-gas differs significantly from syngas, while both gases may vary considerably in their gas mixtures, leading to significant variations in the efficiency of the TBR. Furthermore, due to the inherent limitations of TBRs their end products are not always in a form suitable for processes and products commonly used in the chemical industry.

Other technologies for $CO_2$ fixation include the use of Photo Bio-Reactors (PBR), which contain micro-algae, fed with $CO_2$, CO, glucose, acetate or other fatty acids, organic carbon, etc. for cultivating micro-algae. The cultivated micro-algae is then harvested and used to produce fuels, food supplements, plastics, etc.

On the other hand, PBR known in the prior art rely on the provision of acetate and other products which are sourced from the market and are usually produced from petrochemicals or other source materials that significantly raise costs, and at the same time require the production of more greenhouse gases than those they consume for the cultivation of the micro-algae.

PBR technologies are preferred over race-pond technologies, which are open systems, because their closed-system nature allows better control of their operation and higher productivity. PBRs based on mixotrophy of microalgae (i.e. microalgae that uses a mix of different sources of energy and carbon) using acetate is a well-known concept.

Mixotrophy in PBRs presents the advantages of a higher productivity than autotrophy (i.e. microalgae that uses energy from light to photosynthesize or inorganic chemical reactions—takes $CO_2$ as input and outputs biomass, but has low productivity) and heterotrophy (i.e. microalgae that cannot produce its own food, and relies on taking nutrition from other sources of organic carbon, mainly plant or animal matter) while enabling production of light-dependent biomolecules (e.g. pigments).

However, mixotrophy (takes organic carbon source as input and outputs $CO_2$ and biomass, and has higher productivity than autotrophy) requires an organic carbon source as an input (generally glucose, acetate or glycerol) which represents a big part of the operational costs and which implies a positive $CO_2$ balance of the process.

Furthermore, known TBR and PBR systems need to be maintained, e.g. disinfected and cleaned for avoiding productivity drop, resulting in long downtime and interruption of their operation. For example, TBRs are proposed as typically filled with packing material that provides a higher surface-to-volume ratio. This packing material needs to be regularly cleaned from impurities resulting in the interruption of the operation of the TBR for long periods of time and the disturbance of the microbe culture with negative effects on the TBR operation and its financial implications.

For the reasons, preciously presented, it is obvious to a person skilled in $CO_2$ fixation technologies that a solution to the problem of sustainably boosting $CO_2$ fixation is needed.

SUMMARY

The present innovative solution solves the problem of how to sustainably boost $CO_2$ fixation for growing micro-algae. In a first exemplary embodiment, a system, comprising a Trickle-down Bed Reactor (TdBR), a Photo BioReactor (PBR), and a feedback module is used to sustainably boost $CO_2$ fixation for growing micro-algae. The TdBR comprises a packing material in the form of non-porous particles with a high surface-to-volume ratio, forming a substrate for attachment of Volatile Fatty Acid (VFA) producing microbes. The TdBR and the microbes it contains are fed with $CO_2$ (and/or CO), H2, nutrients, and a moistening liquid for moistening the packing material without soaking or flooding it, for boosting fixation rates and productivity of VFAs. The output of the TdBR, containing VFAs, is fed to the PBR which uses micro-algae modified for increased productivity in the presence of VFAs. No $CO_2$ needs to be fed to the PBA. At least part of the output of the PBA is fed by the feedback module back to the TdBR either as a source of nutrients or for backflushing as a means to unclog the packing material or expulse it from the TdBR for cleaning/ disinfection. The overall $CO_2$ balance of the system operation is negative, while increased productivity is achieved without requiring feeding the system with externally-produced VFAs.

In a second exemplary embodiment, the system of the first exemplary embodiment is modified to include a micro-algae harvester module connected to the output of the PBR. The micro-algae harvester module extracts micro-algae from the liquid output from the PBR and the feedback module takes (in one aspect at least a part of) the effluent liquid full of macronutrients produced by the micro-algae harvester module and fed back to the TdBR either as a source of nutrients or for backflushing as a means to unclog the packing material or expulse it from the TdBR for cleaning/disinfection. The overall $CO_2$ balance of the system operation is negative, while increased productivity is achieved without requiring feeding the system with externally-produced VFAs.

Modifications to the first and second exemplary embodiment of the system are also presented.

A first embodiment of a methodology is executed at the first exemplary embodiment system or at its modifications. The methodology starts by introducing VFA-producing microbes, $CO_2$ (and/or CO), H2, moisturizing liquid and nutrients to a TdBR, followed by introducing in a PBR modified algae, suitable for maximum productivity in a liquid containing VFAs. The TdBR (and the VFA-producing microbes) are allowed to produce a liquid containing VFAs, while continuously (or at intervals) sensing $CO_2$ concentration, and one of more of temperature and pH, in the liquid content of the TdBR, which contains VFAs produced by the VFA-producing microbes. Using the reading(s) of the sensing step the flow of a part of the liquid content of the TdBR (which contains VFAs) into the PBR is adapted, the TdBR is allowed to cultivate the modified micro-algae using the VFAs contained in the liquid content of the TdBR that is supplied to the micro-algae inside the PBR. A part or all of the aqueous solution content of the PBR (which includes micro-algae) is output and selectively fed to either a liquid distribution device of the TdBR as a nutrient, or to a backflush input device of the TdBR for unclogging or cleaning/disinfecting packing material in the TdBR. In the first step of the methodology, syngas or offgas or a combination of the two, containing $CO_2$ is input to the TdBR. Modifications of the first embodiment of the methodology are executed at the first exemplary embodiment system or at its modifications.

A second embodiment of a methodology is executed at the second exemplary embodiment system or at its modifications. In the second embodiment of the methodology, the first embodiment of the methodology is modified to include the step of outputting the aqueous solution content of the TdBR to a micro-algae farming module, which extracts part or all the algae contained in the aqueous solution fed to the algae. The feedback module, then, feeds a part of the effluent liquid, which may still contain micro-algae, from the algae farming module to the TdBR, as nutrient or as backflushing means. Modifications of the second embodiment of the methodology are executed at the second exemplary embodiment system or at its modifications.

DETAILED DESCRIPTION

Figure 1:
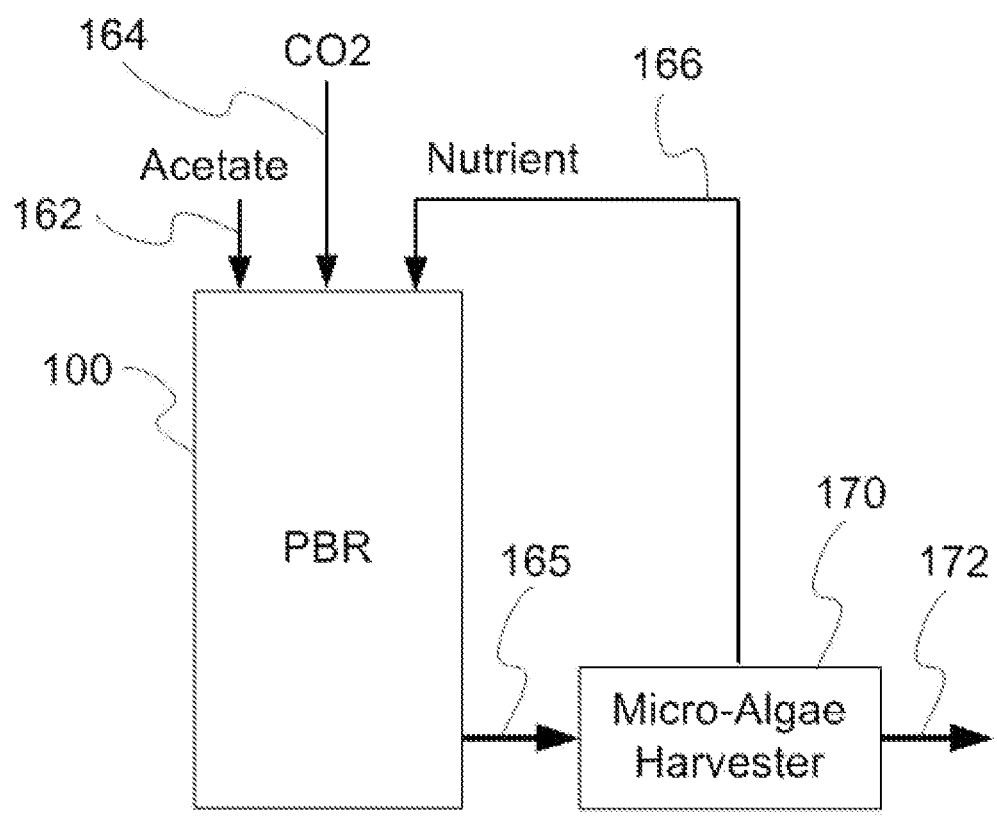
FIG. 1 shows a PBR system according to the prior art.

The word "Any embodiment described herein as "exemplary" is not necessarily to be construed as preferred or advantageous over other embodiments.

The term "exemplary" is used herein to mean "serving as an example, instance, or illustration".

The acronym "ASIC" is intended to mean "Application-Specific Integrated Circuit".

The acronym "CD" is intended to mean "Compact Disc".

The acronym "DSL" is intended to mean "Digital Subscriber Line".

The acronym "DVD" is intended to mean "Digital Versatile Disc".

The acronym "PBR" is intended to mean "Photo BioReactor".

The acronym "TdBR" is intended to mean "Trickle-down Bed Reactor".

The acronym "VFA" is intended to mean "Volatile Fatty Acid".

The acronym "XML" is intended to mean "eXtensible Markup Language".

The term "user" may be used interchangeably with "regular user", "ordinary user", and "client". It may also be used to mean "user of an application" or "user of a device, process, method, or service", unless otherwise explicitly stated or implicitly hinted at in the description, or obvious to a reader of ordinary skill in related art that these terms refer to different things, as this is apparent by the context of the discussion in which they appear.

The term "system" may be used interchangeably with "device", "reactor", "apparatus", "method", and "process", except where it is obvious to a reader of ordinary skill in related art that these terms refer to different things, as this is apparent by the context of the discussion in which they appear. Under any circumstance, and unless otherwise explicitly stated or implicitly hinted at in the description, these six terms should be considered to have the broadest meaning i.e. that of encompassing all six.

The term "module" may be used interchangeably with "unit" or "subunit", except where it is obvious to a reader of ordinary skill in related art that these terms refer to different things, as this is apparent by the context of the discussion in which they appear.

The term "algae" may be used interchangeably with "micro-algae", except where it is obvious to a reader of ordinary skill in related art that these terms refer to different things, as this is apparent by the context of the discussion in which they appear.

The term "liquid" may be used interchangeably with "water", except where it is obvious to a reader of ordinary skill in related art that these terms refer to different things, as this is apparent by the context of the discussion in which they appear.

The term "moistening" is used to mean that an object (e.g. a packing material) is not fully or partially immersed into a liquid, Instead, liquid is put into contact with the surface of the object without immersing it into the liquid.

The term "soaking" is used to mean that an object (e.g. a packing material) is partially immersed into a liquid.

The term "flooding" is used to mean that an object (e.g. a packing material) is completely immersed into a liquid.

As already presented, mixotrophy is more productive than autotrophy but requires an organic carbon source as an input (generally glucose, acetate or glycerol) which represents a big part of the operational costs and which implies a positive CO2 balance of the process.

The present innovative solution is hybrid vertical farming allowing mixotrophy without organic carbon as an input but only CO2 inputted to the first system module (i.e. the TdBR). The organic carbon (as Volatile Fatty Acids) used by the PBR is produced by the system's TdBR. So, the system only required CO2 at its input as a carbon source. This critical aspect differentiates (among other features presented later) the present innovative solution from the prior-art because the CO2 balance of the process becomes negative, while drastically reducing operational costs.

A PBR system for fixating CO2 according to the Prior Art

FIG. 1 shows a PBR system according to the prior art. PBR 100 is typically of the form of a tube, or a set of tubes connected in parallel. PBR 100 has an acetate input 162 for mixotrophy operation, or a CO2 input 164 for autotrophy operation, and a nutrient input 166. Other gases (e.g. CO) and chemicals may also be inputted to PBR 100. PBR 100 also has an output 165, where a liquid containing micro-algae is outputted e.g. to a micro-algae harvester module 170 for extracting micro-algae from the liquid. The microalgae is then outputted at micro-algae harvester output 172 and effluent liquid from micro-algae harvester module 170 is fed back to PBR 170, either at nutrient input 166 or to a feedback input (not shown).

A System for Sustainably Boosting CO2 Fixation for Growing Micro-Algae

First Embodiment

Figure 2:
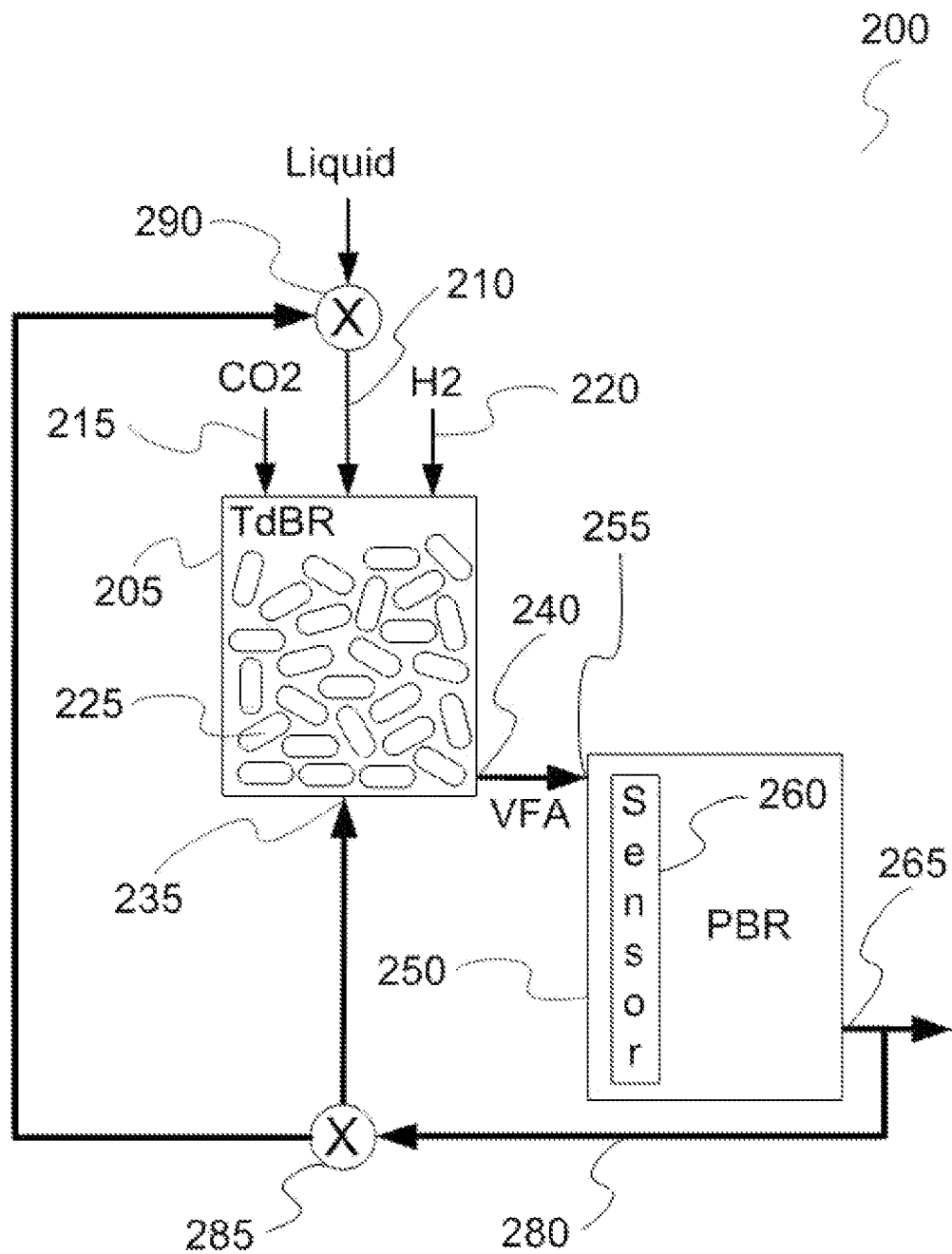
FIG. 2 shows a first embodiment of the present innovative system.

FIG. 2 shows a first embodiment of the present innovative system. System 200 is made up of three main modules: a Trickle-down Bed Reactor (TdBR) 205, a PBR 250, and a feedback module 280.

TdBR 205 has the form of a tube-like structure, or a set of tube-like structures arranged in parallel. In fact, any known TBR can be used in all the embodiments of the present innovative solution, in the place of TdBR 205. The tube-like structures may be formulated in any cross-section or relative dimensions. TdBR 205 has at one end a liquid distribution device 210 for feeding liquid to TdBR 205, an H2 input device 220 for feeding 112, and a CO2 input device 215 for feeding CO2 (and possibly other gasses together with CO2). In one aspect, liquid distribution device 210 is in the form of a sprayer for evenly spraying the liquid to the inside of liquid distribution device 210 so that it trickles down a packing material 225 which partially or fully fills the inside volume of liquid distribution device 210. The aim of liquid distribution device 210 is to spray packing material 225 so that it is always moistened with the liquid while avoiding flooding it. The choice of moistening packing material 225, instead of soaking or flooding it as in the prior art, it made for increasing the productivity of the TdBR.

The increase in the productivity of TdDR 205 is achieved by its design and operation. TdDR 205 is filled with packing material 225, which is selected among known materials for use in acidic environments (e.g. plastic, ceramic, etc.). Packing material 225 is constructed as non-porous particles and formed into any shape that offers a high surface-to-volume ratio. This choice, guarantees that packing material 225 increases the surface onto which bacteria can attach, as opposed to race-pond reactors or TBRs with different types of packing material, and at the same time the lack of pores on its surface prevents clogging and aggregations from nutrients etc. contained in the liquid moistening the packing material and the microbes, that would decrease the gas-liquid contact surface.

Furthermore, microbes are introduced in TdDR 205. In one aspect, the microbes are mixed with the moistening liquid prior to its introduction to TdDR 205. The microbes are mixed microbial consortia, which have selected and/or been enriched and adapted to produce VFAs, while inhibiting Methane or other byproduct production. These modified microbes are selected for maximizing VFA production by maximizing CO2 conversion without the use of chemical catalysts, resulting in maximizing CO2 fixation. The resulting VFAs are then used in PBR 250 as a carbon source to maximize the productivity of micro-algae culturing.

The gas flow can be co-current or counter-current with the liquid medium, which always flows downwards. Both liquid and gas flow pattern is plug-flow. The reactor shape and aspect ratio can be freely chosen (cylindrical or rectangular) as long as the above conditions and adequate wetting of the biofilm are satisfied In one aspect of the present inventive solution, a single species of VFA-producing microbes is used in TdDR 205, while in another aspect, cultures of two or more species of VFA-producing microbes are used. In a third aspect other microbe species may coexist with the VFA-producing microbes in TdDR 205. The presence of other microbes does not create any problem to the present invention as the purpose of TdDR 205 is to produce a liquid containing WA. This VFA-containing liquid is fed to PBR 250 to feed the micro-algae, with the VFA playing the role of carbon source, and thus, the presence of other substances in the liquid does not pose any problem to the cultivation of the modified micro-algae because the micro-algae is modified to be suitable for use in the presence of contaminants, i.e. the byproducts produced by the microbes present in the liquid.

In fact, any algae of mixture of algae can be used in the place of modified algae in all the embodiments of the present innovative solution. In another aspect, any kind of algae (even algae not modified or adapted to acidic conditions) can be used in the exemplary embodiments of the present innovative solution, though at a reduced productivity, e.g. among other things due to lower survival or reproduction rates of the non-selected or adapted/modified micro-algae in acidic conditions.

Furthermore, the WA concentration in the liquid fed to the micro-algae does not pose problems to the productivity of the micro-algae. This is due to the way system 200 operates where the flow of liquid into PBR 250 is adjusted.

The adjustment of the VFA-containing liquid is based not on VFA concentration measurements in the liquid but on its effects on the CO2 concentration, pH level and temperature of the liquid content of PBR 250.

TdBR 205 also has a TdBR output 240 for outputting a liquid containing VFA (and possibly other substances). This liquid is then fed to PBR input 255 of PBR 205.

In one aspect, a VFA reservoir is connected to TdBR output 240 for storing VFAs (and optionally extracting VFAs from the liquid content of TdBR 205, so as to store a liquid with a higher VFA concentration than the VFA concentration in the TdBR output 240).

The liquid content of TdBR 205 may be recirculated back to TdBR 205 (not shown in FIG. 2).

PBR 250 is formed as a tube-like structure (or in another exemplary implementation as a set of tubes connected in parallel) of any cross-section and relative dimensions. PBR 250 is constructed from a transparent material. In another aspect, PBR 250 is partially constructed from a transparent material. The purpose of the transparent material is to allow light (natural and/or artificial) to enter from the outside of the PBR to its liquid content so as to allow mixotrophic cultivation of the algae for enhancing algae productivity.

PBR 250 contains sensory module 260, which has one or more sensors for sensing one or more of the CO2 concentration, pH, and temperature parameters of the liquid inside PBR 250. Based on the sensed CO2 concentration, pH, and temperature, sensory module 260 adjusts the flow of the VFA-containing liquid from TdBR 205 to PBR 250. In one aspect, sensory module 260 adjusts the flow by sending readings of the sensed parameters to a smart pressure-regulating valve at PBR input 255, or to a smart pump. In other aspects, other flow regulating modules are used.

The liquid content of PBR 250 may be recirculated into PBR 250 by feeding it from PBR output 265 back to the PBR 250 (not shown in FIG. 2) for further enhancing algae productivity by increasing algal exposure to light for enhancing photoautotrophic metabolism. In one aspect, the recirculated liquid is fed back to a PBR feedback input (not shown in FIG. 2), while in other aspects it is fed back to PBR input 255.

In an alternative exemplary embodiment, the liquid content of PBR 250 is not recirculated in PBR 250.

In yet another exemplary embodiment, a stirring module inside PBR 250 stirs the liquid content of the PBR for further enhancing algae productivity by increasing algal exposure to light for enhancing photoautotrophic metabolism.

Feedback module 280, is connected to PBR output 265 and feeds part of the liquid content of PBR 250 to TBR 205. Feedback module 280 may use a pump or other similar module (not shown in FIG. 2) and operate in one of two modes.

In a first mode of operation, the "nutrient feedback operation mode", feedback module 280 feeds a part of the liquid content of PBR 250 to TdBR's 205 liquid distribution device 210, where the fed-back liquid is used as nutrient by the VFA-producing microbes inside TdBR 205, effectively boosting their productivity while at the same time reducing or eliminating the need to externally supply nutrients to TdBR 205.

In a second mode of operation, the "backflush operation mode", feedback module 280 feeds a part of the liquid content of PBR 250 to TdBR's 205 backflush input 210, where the fed-back liquid is used to reverse the flow inside TBR 205. This flow reversal ensures that any nutrient or other coagulations formed on packing material 225 are dissolved and the trickle-down flow of the moisturizing liquid will not be obstructed during nutrient feedback operation mode. Although the design of system's 200 TBR 205 prevents such clogging, clogging may occasionally be formed after very prolonged operation of system 200. By means of example and without limiting the scope of protection of the present invention, the backflush operation mode may be needed after several hundred or thousand hours of operation and may depend on the type of nutrients fed into TBR 205 and the size and shape of packing material 325.

The backflush operation mode may also be used to expulse packing material outside TdBR 205 (through an opening not shown in FIG. 2) for cleaning or disinfection. Although it is not needed to clean or disinfect TdBR 205, this option is available if system 200 is used under different operating conditions and using single or multi-culture microbes under aseptic conditions.

PBR output 265, may in other exemplary embodiments be used only for outputting the algae containing liquid of PBR 250, either continuously or in batches, outside of system 200. In such exemplary embodiments, the liquid content of PBR 250 is recirculated into PBR 250, and/or fed back to TdBR 205 from a separate output(s) (not shown in FIG. 2).

The use of feedback module 280 and the nutrient feedback and backflush operation modes, ensure sustainable increased productivity at reduced costs, and uninterrupted operation in non-open systems, respectively.

The operation of feedback module 280, is achieved by a valve 285 connected at a bifurcation of a main feedback pipe. Valve 285 can be set to open either the bifurcation connected to liquid distribution device 210, while closing the bifurcation connected to feedback input device 235, or to close the bifurcation connected to liquid distribution device 210, while opening the bifurcation connected to feedback input device 235. In such a setup, when the bifurcation connected to liquid distribution device 210 is open, a liquid distribution input valve 290 is also opened to allow the feedback liquid to enter TdBR 205. Valve 290 is closed when valve 285 closes the bifurcation connected to liquid distribution device 210 so that to prevent the liquid (externally to system 200) inputted to TdBR 205 from flowing in reverse flow into feedback module 180.

The orientation and the relative positions of the modules of system 200 may differ from those shown in FIG. 2 without departing from the scope of protection of the present invention. The vertical orientation of TdBR 205 is preferred for optimizing moistening of packing material 225 with a liquid distribution module 210 (e.g. in the form of a single uniform spay-type or rinsing-type design, and for minimizing the trickle down onto TdBR 205 tube's internal surface but onto the surface of the packing material, thereby saving on the operation costs of the system as lower amounts of liquid are required to be pumped from feeding TdBR 205) while maximizing use of the moistening liquid and avoiding flooding part of packing material 225, which would result in TBR 205 productivity drop.

The CO2 fed to CO2 input device 215 may be sourced from any available source. By means of example, CO2 may be "clean" CO2 isolated from offgas or syngas, or other gas mixtures. In another aspect, the CO2 may simply be in a mixture of other gasses (e.g. one including CO), which is supplied from an offgas or syngas source. The presence of other gases (except O2) together with the CO2 does not cause any problems in the operation of TdBR 205 as the VFA producing microbes are resistant and/or benefit from the supply of gases other than CO2. This feature of the VFA-producing microbes is used to the benefit of the system's 200 operation of the TdBR 205, by eliminating the need to include a process step to isolate CO2.

In an exemplary embodiment, system 200 operates with CO2 contained in a syngas or offgas mixture, which has been preconditioned. Such a preconditioning step is a standard process used by virtually every producer of such gasses (e.g. industrial installations) due to environmental regulations existing in virtually all countries. Although such regulations differ among countries, and although environmental regulations may change over time, it is highly unlikely, if not impossible, that any such regulations will be abolished in the near future (or at least for the life of the present application and patent) or even relaxed due to the greenhouse effect of CO2 and other gasses and the serious environmental problems they pose by causing global warming. For these reasons, the preconditioning step of syngas and offgas may be considered de facto and not needed to be performed by system 200, or at least be considered an optional step.

In another aspect, such a preconditioning step may be tuned for producing gas mixtures of a certain CO2 concentration. Examples, non-limiting the scope of protection of the present invention, include one of:
 45% H2, 20% CO, 25% CO2 vol.
 67% H2 and 33% CO2 vol. for full conversion of CO2 and H2 in offgas
 a syngas mixture with a Syngas Quality Index (SQI) of 2, where SQI=(% H2+% CO)/(% CO2+% CO) vol.
 any composition of up to 20-40% CO2 vol.

During the preconditioning step, hot syngas and/or offgas effectively cools to a much lower temperature (e.g. 5-80° C.) either as the effect of heat loss to the surrounding atmosphere, or as an active cooling process, e.g. with the use of a heat exchanger. Preconditioned gasses at these temperatures can be directly fed to system 200 without further cooling.

In yet another exemplary implementation, only TdBR's 205 CO2 input device 215 has a heat exchange module that cools input syngas or offgas at a temperature approximately within the 5-80° C., which is the operating temperature of TdBR 205, dictated by the VFA-producing microbes' tolerance to heat.

In a preferential exemplary implementation, TdBR 205 is operated at approximately 55-80° C. for achieving increased productivity of the VFA-producing microbes.

The VFA containing liquid outputted from TdBR's 205 output 240 is fed directly to PBR's 250 input 255 without cooling it, despite the fact that the micro-algae of PBR 250 can only withstand temperatures of 5-40° C. However, as the flow of VFA-containing liquid into PBR's 250 input 255 is very low compared to the flow of the liquid inside PBR 250, i.e. recirculation of the liquid of PBR 250, resulting in a very low concentration of VFAs in PBR 250 (e.g. 1 lt of VFA-containing liquid per 1000 lt of liquid content of PBR 250, or other low concentration), the VFA-containing liquid is very quickly cooled to the temperature of the PBR liquid containing the micro-algae and as a result the micro-algae is not killed by the inputted VFA-containing liquid, despite its higher temperature, outside the acceptable range for the micro-algae. An additional advantage of this system design is that there is no need to have a heat exchange module at PBR 250.

It is understood by persons skilled in related art, that system 200 is presented by means of example and that alternative implementations and modes of operation, that are equivalent or have the same or equivalent technical effect fall within the scope of protection of the present invention. It is also assumed that obvious or equivalent modifications, the merging or splitting of modules, as well as, the inclusion of additional but obvious modules and apparatuses (e.g. valves, pumps, cabling, microcontrollers, microprocessors, etc.) not shown in the figures, also fall within the scope of protection of the present invention. These also hold true for the alternative exemplary implementations presented below.

Second Embodiment

Figure 3:
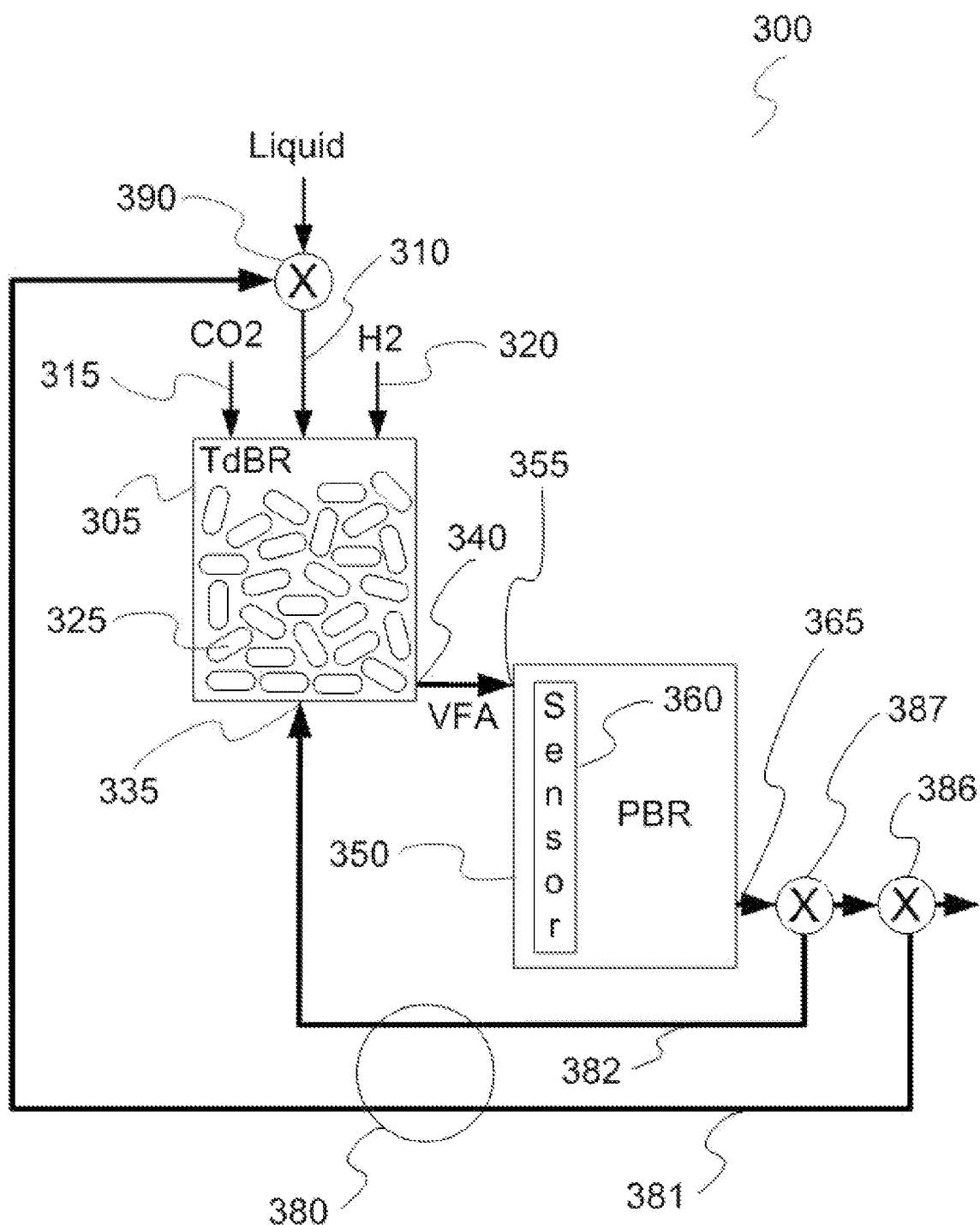
FIG. 3 shows a second embodiment of the present innovative system.

FIG. 3 shows a second embodiment of the present innovative system. System 300 is made up of three main modules: a Trickle-down Bed Reactor (TdBR) 305, a PBR 350, and a feedback module 380.

TdBR 305 has the form of a tube-like structure, or a set of tube-like structures connected in parallel. The tube-like structures may be formed in any cross-section or relative dimensions. TdBR 305 has at one end a liquid distribution device 310 for feeding liquid to TdBR 305, a feedback input device an H2input device 320 for feeding H2, and a CO2 input device 315 for feeding CO2 (and possibly other gasses together with CO2). In one aspect, liquid distribution device 310 is in the form of a sprayer for evenly spraying the liquid to the inside of liquid distribution device 310 so that it trickles down a packing material 325, which partially or fully fills the inside volume of liquid distribution device 310. The aim of liquid distribution device 310 is to spray packing material 325 so that it is always moistened with the liquid while avoiding flooding it. The choice of moistening packing material 325, instead of soaking or flooding it as in the prior art, is made for increasing the productivity of TdBR 305.

Furthermore, VFA-producing microbes are introduced in TdDR 305. In one aspect, the microbes are mixed with the moistening liquid prior to its introduction to TdDR 305.

TdBR 305 also has a TdBR output 340 for outputting a liquid containing VFA (and possibly other substances). This liquid is then fed to PBR input 355 of PBR 305.

The liquid content of TdBR 305 may be recirculated back to TdBR 305 (not shown in FIG. 3).

The resulting VFAs are suspended in a VFA-containing liquid and are then used in PBR 350 as a carbon source to maximize the productivity of micro-algae culturing.

PBR 350 is formed as a tube-like structure (or in another exemplary implementation as a set of tubes connected in parallel) of any cross-section and relative dimensions. PBR 350 is constructed from a transparent material. In another aspect, PBR 350 is partially constructed from a transparent material. The purpose of the transparent material is to allow light (natural and/or artificial) to enter from the outside of the PBR to its liquid content so as to allow mixotrophic cultivation of the micro-algae for enhancing algae productivity.

PBR 350 contains sensory module 360, which has one or more sensors for sensing one or more of the CO2 concentration, pH, and temperature parameters of the liquid inside PBR 350. Based on the sensed CO2 concentration, pH, and temperature, sensory module 360 adjusts the flow of the VFA-containing liquid from TdBR 305 to PBR 350. In one aspect, sensory module 360 adjusts the flow by sending readings of the sensed parameters to a smart pressure-regulating valve at PBR input 355, or to a smart pump. In other aspects, other flow regulating modules are used.

The liquid content of PBR 350 may be recirculated into PBR 350 by feeding it from PBR output 365 back to the PBR 300 (not shown in FIG. 3) for further enhancing algae productivity by increasing algal exposure to light for enhancing photoautotrophic metabolism. In one aspect, the recirculated liquid is fed back to a PBR feedback input (not shown in FIG. 3), while in other aspects it is fed back to PBR input 355.

In an alternative exemplary embodiment, the liquid content of PBR 350 is not recirculated in PBR 350.

In yet another exemplary embodiment, a stirring module inside PBR 350 stirs the liquid content of the PBR for further enhancing algae productivity by increasing algal exposure to light for enhancing photoautotrophic metabolism Feedback module 380, is connected to PBR output 365 and feeds part of the liquid content of PBR 350 to TBR 305. Feedback module 380 has two independent feedback sub-modules 381, 382. Feedback sub-module 381 is connected, via valve 386, to liquid distribution device 310 for supplying liquid as nutrient from the PBR's 350 output 365 to TdBR's 305 liquid distribution device 310, and feedback sub-module 382 is connected, via valve 387, to TdBR's 305 feedback input device 335 for supplying liquid as backflush medium from PBR's 350 output 365 to TdBR's 305 feedback input device 235. In the embodiment of FIG. 3 there is no bifurcation in the feedback pike (and no valve at a bifurcation point. A valve may be used at the liquid distribution device 390 and/or at the points where the feedback sub-modules are attached to output 364 of PBR 350.

Feedback module 380 may use a pump or other similar module (not shown in FIG. 2) and operate in one of two modes.

In a modification of the present exemplary embodiment, independent feedback sub-modules 381, 382 are both connected to biomass harverster 350, which contains valves 386, 387. This modification is not shown in FIG. 3.

In a first mode of operation, the "nutrient feedback operation mode", feedback module 380 feeds a part of the liquid content of PBR 350 to TdBR's 305 liquid distribution device 310, where the fed-back liquid is used as nutrient by the VFA-producing microbes inside TdBR 305, effectively boosting their productivity while at the same time reducing or eliminating the need to externally supply nutrients to TdBR 305.

In a second mode of operation, the "backflush operation mode", feedback module 380 feeds a part of the liquid content of PBR 350 to TdBR's 305 backflush input 310, where the fed-back liquid is used to reverse the flow inside TBR 305. This flow reversal ensures that any nutrient or other coagulations formed on packing material 325 are dissolved and the trickle-down flow of the moisturizing liquid will not be obstructed during nutrient feedback operation mode. Although the design of system's 300 TBR 305 prevents such clogging, clogging may occasionally be formed after very prolonged operation of the system 300. By means of example and without limiting the scope of protection of the present invention, the backflush operation mode may be needed after several hundred or thousand hours of operation and may depend on the type of nutrients fed into TBR 305 and the size and shape of packing material 325.

The backflush operation mode may also be used to expulse packing material outside TdBR 305 (through an opening not shown in FIG. 3) for cleaning or disinfection. Although it not needed to clean or disinfect TdBR 305, this option is available if system 300 is used under different operating conditions and using single or multi-culture microbes under aseptic conditions PBR output 365, may in other exemplary embodiments be used only for outputting the algae containing liquid of PBR 350, either continuously or in batches, outside of system 300. In such exemplary embodiments, the liquid content of PBR 350 is recirculated into PBR 350, and/or fed back to TdBR 305 from a separate output(s) (not shown in FIG. 3).

The VFA containing liquid outputted from TdBR's 305 output 340 is fed directly to PBR's 350 input 355 without cooling it, despite the fact that the micro-algae of PBR 350 can only withstand temperatures of 5-40° C. However, as the flow of VFA-containing liquid into PBR's 350 input 355 is very low compared to the flow of the liquid inside PBR 350, i.e. recirculation of the liquid of PBR 350, resulting in a very low concentration of VFAs in PBR 350 (e.g. 1 lt of VFA-containing liquid per 1000 lt of liquid content of PBR 350, or other low concentration), the VFA-containing liquid is very quickly cooled to the temperature of the PBR liquid containing the micro-algae and as a result the micro-algae is not killed by the inputted VFA-containing liquid, despite its higher temperature, outside the acceptable range for the micro-algae. An additional advantage of this system design is that there is no need to have a heat exchange module at PBR 350.

The use of feedback module 380 and the nutrient feedback and backflush operation modes, ensure sustainable increased productivity at reduced costs, and uninterrupted operation in non-open systems, respectively.

The design and operation of the second embodiment is identical with the first embodiment, except to what concerns the use of two individual feedback sub-modules in the second embodiment, as opposed to the single bifurcated feedback module of the first embodiment.

Third Embodiment

Figure 4:
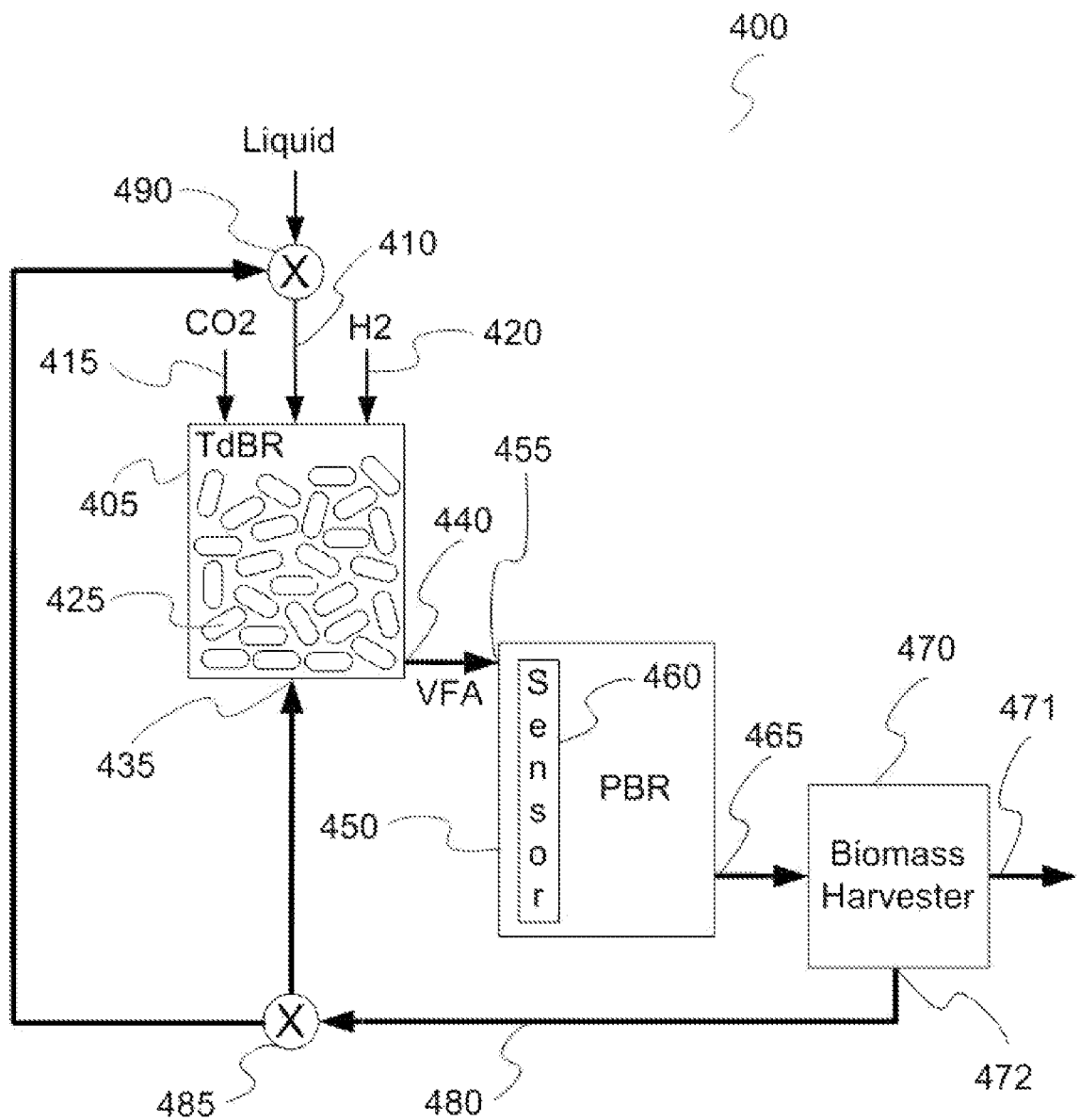
FIG. 4 shows a third embodiment of the present innovative system.

FIG. 4 shows a third embodiment of the present innovative system. System 430 is made up of three main modules: a Trickle-down Bed Reactor (TdBR) 405, a PBR 450, and a feedback module 480.

TdBR 405 has the form of a tube-like structure, or a set of tube-like structures arranged in parallel. The tube-like structures may be formulated in any cross-section or relative dimensions. Has at one end a liquid distribution device 410 for feeding liquid to TdBR 405, a feedback input device an 112 input device 420 for feeding 112, and a CO2 input device 415 for feeding CO2 (and possibly other gasses together with CO2). In one aspect, liquid distribution device 410 is in the form of a sprayer for evenly spraying the liquid to the inside of liquid distribution device 410 so that it trickles down a packing material 425 which partially or fully fills the inside volume of liquid distribution device 410. The aim of liquid distribution device 410 is to spray packing material 425 so that it is always moistened with the liquid while avoiding flooding it. The choice of moistening packing material 425, instead of soaking or flooding it as in the prior art, it made for increasing the productivity of the TdBR.

Furthermore, VFA-producing microbes are introduced in TdDR 405. In one aspect, the microbes are mixed with the moistening liquid prior to its introduction to TdDR 405.

TdBR 405 also has a TdBR output 440 for outputting a liquid containing VFA (and possibly other substances). This liquid is then fed to PBR input 455 of PBR 405.

The liquid content of TdBR 405 may be recirculated back to TdBR 405 (not shown in FIG. 4).

The resulting VFAs are suspended in a VFA-containing liquid and are then used in PBR 450 as a carbon source to maximize the productivity of micro-algae culturing.

PBR 450 is formed as a tube-like structure (or in another exemplary implementation as a set of tubes connected in parallel) of any cross-section and relative dimensions. PBR 450 is constructed from a transparent material. In another aspect, PBR 450 is partially constructed from a transparent material. The purpose of the transparent material is to allow light (natural and/or artificial) to enter from the outside of the PBR to its liquid content so as to allow mixotrophic cultivation of the algae for enhancing algae productivity.

PBR 450 contains sensory module 460, which has one or more sensors for sensing one or more of the CO2 concentration, pH, and temperature parameters of the liquid inside PBR 450. Based on the sensed CO2 concentration, pH, and temperature, sensory module 460 adjusts the flow of the VFA-containing liquid from TdBR 405 to PBR 450. In one aspect, sensory module 460 adjusts the flow by sending readings of the sensed parameters to a smart pressure-regulating valve at PBR input 455, or to a smart pump. In other aspects, other flow regulating modules are used.

The liquid content of PBR 450 may be recirculated into PBR 450 by feeding it from PBR output 465 back to PBR 450 (not shown in FIG. 4) for further enhancing algae productivity by increasing algal exposure to light for enhancing photoautotrophic metabolism. In one aspect, the recirculated liquid is fed back to a PBR feedback input (not shown in FIG. 4), while in other aspects it is fed back to PBR input 455.

In an alternative exemplary embodiment, the liquid content of PBR 450 is not recirculated in PBR 450.

PBR 450 is connected from its PBR output 465 to a biomass-harvester module 470 which uses a method known in the art (e.g. centrifugation, mechanical collection and extraction, straining, etc.). Biomass-harvester module 470 outputs biomass (i.e. isolated micro-algae, or biomass mixed with other elements present in the liquid content of PBR 450), via biomass output 471, for use external to system 400. This outputted biomass can be used unprocessed (e.g. as nutrient, etc.) outside of system 400, or by any external system which processes the biomass for producing other products (e.g. dried algae for easy storage, biofuels, food supplements, etc.).

Biomass-harvester module 470 also has an effluent output 472, which outputs the effluent liquid, which remains after the extraction of micro-algae from the liquid content of PBR 450. This effluent liquid may contain algae at lower concentrations compared to the liquid content of PBR 450), and other contents (which were contained in the liquid content of PBR 450 and which were not removed by biomass-harvester module 470. In another aspect, the effluent liquid may have identical content to the liquid content of PBR 450, if biomass-harvester module 470 does not extract biomass from the liquid it receives from PBR's output 465.

It is understood, and is obvious to persons of skill in related art, that biomass-harvester module 470 may also contain other elements, like valves, pumps, strainers, mechanical collector elements, etc. which are not shown in FIG. 4.

Feedback module 480, is connected to harvester module's 470 effluent output 472 for receiving the effluent liquid and feeding it to TBR 405. Feedback module 480 may use a pump or other similar module (not shown in FIG. 4) and operate in one of two modes.

In a first mode of operation, the "nutrient feedback operation mode", feedback module 480 feeds the effluent liquid from harvester module's 470 to TdBR's 405 liquid distribution device 410, where the fed-back liquid is used as nutrient by the VFA-producing microbes inside TdBR 405, effectively boosting their productivity while at the same time reducing or eliminating the need to externally supply nutrients to TdBR 405.

In a second mode of operation, the "backflush operation mode", feedback module 480 feeds a part of the liquid content of PBR 450 to TdBR's 405 backflush input 435, where the fed-back liquid is used to reverse the flow inside TBR 405. This flow reversal ensures that any nutrient or other solid coagulations formed on packing material 425 are broken or dissolved and the trickle-down flow of the moisturizing liquid will not be obstructed during nutrient feedback operation mode. Although the design of system's 400 TBR 405 prevents such clogging, clogging may occasionally be formed after very prolonged operation of the system 400. By means of example and without limiting the scope of protection of the present invention, the backflush operation mode may be needed after several hundred or thousand hours of operation and may depend on the type of nutrients fed into TBR 405 and the size and shape of packing material 425.

The backflush operation mode may also be used to expulse packing material outside TdBR 405 (through an expulsion output not shown in FIG. 4) for cleaning or disinfection. Although it not needed to clean or disinfect TdBR 405, this option is available if system 400 is used under different operating conditions and using single or multi-culture microbes under aseptic conditions.

Biomass harvester's 470 output 471, may in other exemplary embodiments be used only for outputting the harvested algae containing liquid of PBR 450, either continuously or in batches, outside of system 400. In such exemplary embodiments, the liquid content of PBR 450 is recirculated into PBR 450, and/or fed back to TdBR 405 from a separate output(s) (not shown in FIG. 4).

The use of feedback module 480 and the nutrient feedback and backflush operation modes, ensure sustainable increased productivity at reduced costs, and uninterrupted operation in non-open systems, respectively.

The operation of feedback module 480, is achieved by a valve 485 connected at a bifurcation of a main feedback pike. Valve 485 can be set to open either the bifurcation connected to liquid distribution device 410, while closing the bifurcation connected to feedback input device 435, or to close the bifurcation connected to liquid distribution device 410, while opening the bifurcation connected to feedback input device 435. In such a setup, when the bifurcation connected to liquid distribution device 410 is open, a liquid distribution input valve 490 is also opened to allow the feedback liquid to enter TdBR 405. Valve 490 is closed when valve 485 closes the bifurcation connected to liquid distribution device 410 so as to prevent the liquid (externally to system 200) inputted to TdBR 405 from flowing in reverse flow into feedback module 480.

The orientation and the relative positions of the modules of system 400 may differ from those shown in FIG. 4 without departing from the scope of protection of the present invention. The vertical orientation of TdBR 405 is preferred for optimizing moistening of packing material 425 with a liquid distribution module 410 (e.g. in the form of a single uniform spay-type or rinsing-type design) while maximizing use of the moistening liquid and avoiding flooding part of packing material 425, which would result in TBR 405 productivity drop.

The CO2 fed to CO2 input device 415 may be sourced from any available source. By means of example, it may be "clean" CO2 isolated from offgas or syngas, or other gas mixtures. In another aspect, the CO2 may simply be in a mixture of other gasses (e.g. one including CO), which is supplied from an offgas or syngas source. The presence of other gases together with the CO2 does not cause any problems in the operation of TdBR 405 as the VFA producing microbes are resistant and/or benefit from the supply of gases other than CO2. This feature of the VFA-producing microbes is used to the benefit of the system's 400 operation of the TdBR 405, by eliminating the need to include a process step to isolate CO2.

In an exemplary embodiment, system 400 operates with CO2 contained in a syngas or offgas mixture, which has been preconditioned. Such a preconditioning step is a standard process used by virtually every producer of such gasses (e.g. industrial installations) due to environmental regulations existing in virtually all countries.

Although such regulations differ among countries, and although environmental regulations may change over time, it is highly unlikely, if not impossible, that any such regulations will be abolished in the near future (or at least for the life of the present application and patent) or even relaxed due to the greenhouse effect of CO2 and other gasses and the serious environmental problems they pose by causing global warming. For these reasons, the preconditioning step of syngas and offgas may be considered de facto and not needed to be performed by system 400.

In another aspect, such a preconditioning step may be tuned for producing gas mixtures a certain CO2 concentration. Examples, non-limiting the scope of protection of the present invention, include the following gas mixtures:
- 45% H2, 20% CO, 25% CO2 vol.
- 67% H2 and 33% CO2 vol. for full conversion of CO2 and H2 in offgas
- a syngas mixture with a Syngas Quality Index (SQI) of 2, where SQI=(% H2+% CO)/(% CO2+CO) vol.
- any composition of up to 20-40% CO2 vol.

During the preconditioning step, hot syngas and/or offgas effectively cools to a much lower temperature (e.g. 5-80° C.) either as the effect of heat loss to the surrounding atmosphere, or as an active cooling process, e.g. with the use of a heat exchanger. Preconditioned gasses at these temperatures can be directly fed to system 400 without further cooling.

In yet another exemplary implementation, only TdBR's 405 CO2 input device 415 has a heat exchange module that cools input syngas or offgas at a temperature approximately within the 5-80° C., which is the operating temperature of TdBR 405, dictated by the VFA-producing microbes' tolerance to heat.

In another exemplary implementation, TdBR's 405 CO2 input device 415 does not have a heat exchange module to cool the inputted syngas or offgas at a temperature approximately within the 5-80° C. Such a heat exchange module is not needed as the effluent liquid, fed by feedback module 480 from biomass harvester module 470 to TdBR 405, is already at a lower temperature than the CO2-containing gas (offgas, or syngas, etc.) and together with the existing liquid content of TdBR 405 result in coiling the CO2-containing gas. The heat conveyed by the CO2-containing gas to the liquid content of TdBR 405 is dissipated by convection and radiation from TdBR 405, the pipes connecting TdBR 405 to PBR 450, and the pipes recirculating TdBR's 405 liquid content back to TdBR 405. This heat dissipate is enough to allow the temperature inside TdBR 405 to stay relatively stable and in any case within its operating temperature range of 5-80° C.

In an alternative exemplary implementation one or more heat exchange module is added to TdBR 405 or the pipes connecting TdBR 405 with the CO2, H2, nutrient and liquid feedback supplies. Such a heat exchange module may be used either for accurately regulating the operating temperature inside TdBR 405 (e.g. to a preferential narrow operating temperature range for increasing TdBR 405 productivity) or for inputting CO2 gas (or CO2 gas mixtures) to TdBR 405 at temperatures at least 50% higher than the maximum operating temperature of TdBR 405.

In a preferential exemplary implementation, TdBR 405 is operated at approximately 60-80° C. for achieving increased productivity of the VFA-producing microbes.

The VFA containing liquid outputted from TdBR's 405 output 440 is fed directly to PBR's 450 input 455 without cooling it, despite the fact that the micro-algae of PBR 450 can only withstand temperatures of 5-40° C. However, as the flow of VFA-containing liquid into PBR's 450 input 455 is very low compared to the flow of the liquid inside PBR 450, i.e. recirculation of the liquid of PBR 450, resulting in a very low concentration of VFAs in PBR 450 (e.g. 1 lt of VFA-containing liquid per 1000 lt of liquid content of PBR 450), the VFA-containing liquid is very quickly cooled to the temperature of the PBR liquid containing the micro-algae and as a result the micro-algae is not killed by the inputted VFA-containing liquid, despite its higher temperature, outside the acceptable range for the micro-algae. An additional advantage of this system design is that there is no need to have a heat exchange module at PBR 450.

It is understood by persons skilled in related art, that system 400 is presented by means of example and that alternative implementations and modes of operation, that are equivalent or have the same or equivalent technical effect fall within the scope of protection of the present invention. It is also assumed that obvious or equivalent modifications, the merging or splitting of modules, as well as, the inclusion of additional but obvious modules and apparatuses (e.g. valves, pumps, cabling, microcontrollers, microprocessors, etc.) not shown in the figures, also fall within the scope of protection of the present invention. These also hold true for the alternative exemplary implementations presented below.

In yet another exemplary embodiment, a stirring module inside PBR 450 stirs the liquid content of the PBR for further enhancing algae productivity by increasing algal exposure to light for enhancing photoautotrophic metabolism.

The design and operation of the third embodiment is identical with the first embodiment, except to what concerns the addition of biomass harvester 490.

Fourth Embodiment

Figure 5:
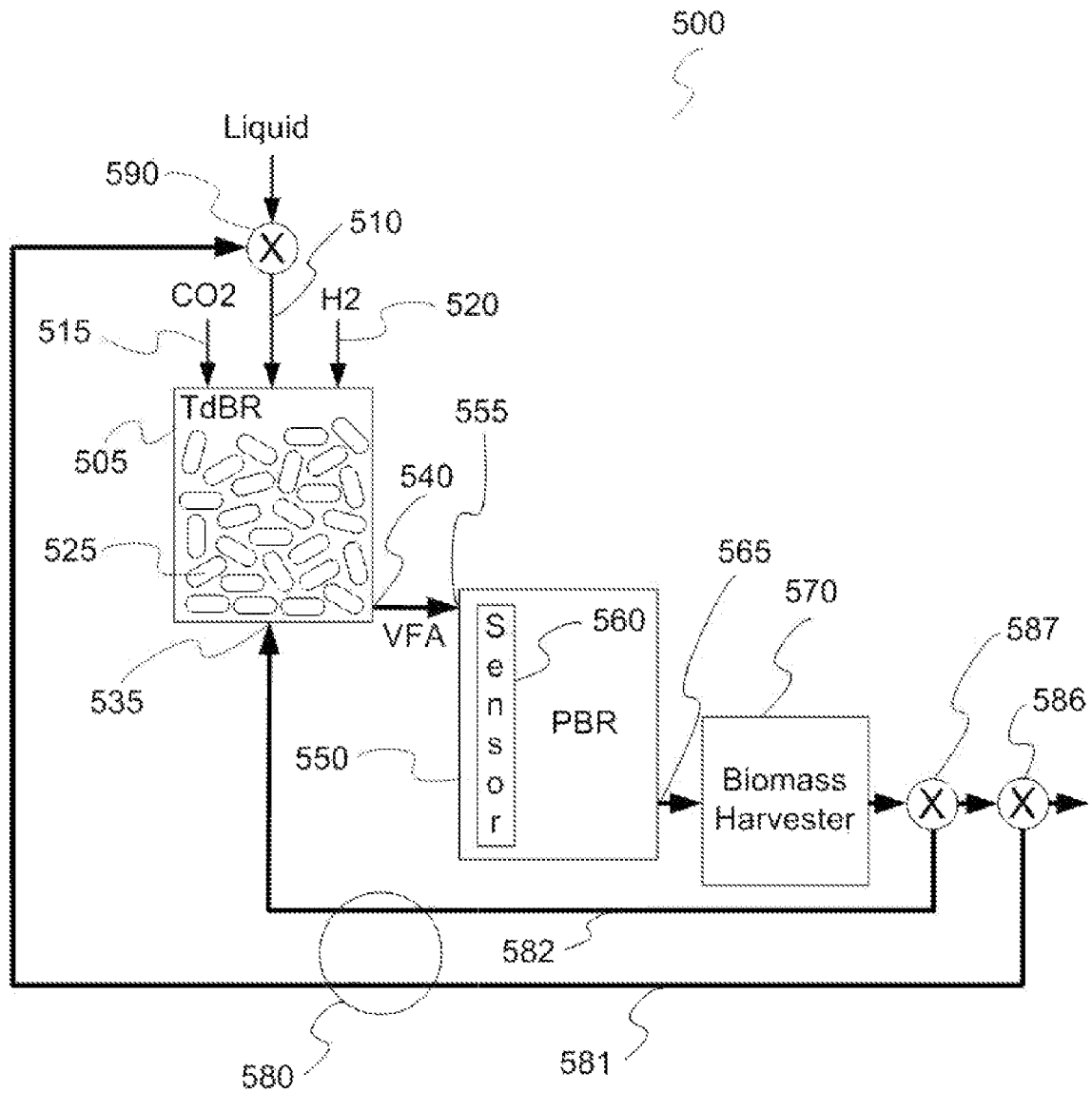
FIG. 5 shows a fourth embodiment of the present innovative system.

FIG. 5 shows a fourth embodiment of the present innovative system. System 530 is made up of three main modules: a Trickle-down Bed Reactor (TdBR) 505, a PBR 550, and a feedback module 580.

TdBR 505 has the form of a tube-like structure, or a set of tube-like structures arranged in parallel. The tube-like structures may be formulated in any cross-section or relative dimensions. Has at one end a liquid distribution device 510 for feeding liquid to TdBR 505, a feedback input device an H2 input device 520 for feeding H2, and a CO2 input device 515 for feeding CO2 (and possibly other gasses together with CO2). In one aspect, liquid distribution device 510 is in the form of a sprayer for evenly spraying the liquid to the inside of liquid distribution device 510 so that it trickles down a packing material 525 which partially or fully fills the inside volume of liquid distribution device 510. The aim of liquid distribution device 510 is to spray packing material 525 so that it is always moistened with the liquid while avoiding flooding it. The choice of moistening packing material 525, instead of soaking or flooding it as in the prior art, it made for increasing the productivity of the TdBR.

Furthermore, VFA-producing microbes are introduced in TdDR 505. In one aspect, the microbes are mixed with the moistening liquid prior to its introduction to TdDR 505.

TdBR 505 also has a TdBR output 540 for outputting a liquid containing VFA (and possibly other substances). This liquid is then fed to PBR input 555 of PBR 505.

The liquid content of TdBR 505 may be recirculated back to TdBR 505 (not shown in FIG. 5).

The resulting VFAs are suspended in a VFA-containing liquid and are then used in PBR 550 as a carbon source to maximize the productivity of micro-algae culturing.

PBR 550 is formed as a tube-like structure (or in another exemplary implementation as a set of tubes connected in parallel) of any cross-section and relative dimensions. PBR 550 is constructed from a transparent material. In another aspect, PBR 550 is partially constructed from a transparent material. The purpose of the transparent material is to allow light (natural and/or artificial) to enter from the outside of the PBR to its liquid content so as to allow mixotrophic cultivation of the algae for enhancing algae productivity.

PBR 550 contains sensory module 560, which has one or more sensors for sensing one or more of the CO2 concentration, pH, and temperature parameters of the liquid inside PBR 550. Based on the sensed CO2 concentration, pH, and temperature, sensory module 560 adjusts the flow of the VFA-containing liquid from TdBR 505 to PBR 550. In one aspect, sensory module 460 adjusts the flow by sending readings of the sensed parameters to a smart pressure-regulating valve at PBR input 555, or to a smart pump. In other aspects, other flow regulating modules are used.

The liquid content of PBR 550 may be recirculated into PBR 550 by feeding it from PBR output 565 back to PBR 550 (not shown in FIG. 5) for further enhancing algae productivity by increasing algal exposure to light for enhancing photoautotrophic metabolism. In one aspect, the recirculated liquid is fed back to a PBR feedback input (not shown in FIG. 5), while in other aspects it is fed back to PBR input 555.

In an alternative exemplary embodiment, the liquid content of PBR 550 is not recirculated in PBR 550.

PBR 550 is connected from its PBR output 465 to a biomass-harvester module 570 which uses a method known in the art (e.g. centrifugation, mechanical collection and extraction, straining, etc.). Biomass-harvester module 570 outputs biomass (i.e. isolated micro-algae, or biomass mixed with other elements present in the liquid content of PBR 550), via biomass output 571, for use external to system 500. This outputted biomass can be used unprocessed (e.g. as nutrient, etc.) outside of system 500, or by any external system which processes the biomass for producing other products (e.g. dried algae for easy storage, biofuels, food supplements, etc.).

Biomass-harvester module 570 also has an effluent output 572, which outputs the effluent liquid, which remains after the extraction of micro-algae from the liquid content of PBR 550. This effluent liquid may contain algae at lower concentrations compared to the liquid content of PBR 550), and other contents (which were contained in the liquid content of PBR 550 and which were not removed by biomass-harvester module 570. In another aspect, the effluent liquid may have identical content to the liquid content of PBR 550, if biomass-harvester module 570 does not extracted biomass from the liquid it receives from PBR's output 565.

It is understood, and is obvious to persons of skill in related art, that biomass-harvester module 570 may also contain other elements, like valves, pumps, strainers, mechanical collector elements, etc. which are not shown in FIG. 5.

Feedback module 580, is connected to harvester module's 570 effluent output 572 for receiving the effluent liquid and feeding it to TBR 505.

Feedback module 580 has two independent feedback sub-modules 581, 582. Feedback sub-module 581 is connected, via valve 386, to liquid distribution device 510 for supplying liquid as nutrient from the PBR's 550 output 565 to TdBR's 505 liquid distribution device 510, and feedback sub-module 582 is connected, via valve 587, to TdBR's 505 feedback input device 535 for supplying liquid as backflush medium from PBR's 550 output 565 to TdBR's 505 feedback input device 535. In the embodiment of FIG. 5 there is no bifurcation in the feedback pike (and no valve at a bifurcation point. A valve may be used at the liquid distribution device 590 and/or at the points where the feedback sub-modules are attached to output 564 of PBR 550.

Feedback module 580 may use a pump or other similar module in each feedback sub-module 582, 584 (not shown in FIG. 5) and operate in one of two modes.

In a modification of the present exemplary embodiment, independent feedback sub-modules 581, 582 are both connected to biomass harverster 550, which contains valves 586, 587. This modification is not shown in FIG. 5.

In a first mode of operation, the "nutrient feedback operation mode", feedback module 580 feeds the effluent liquid from harvester module's 570 to TdBR's 505 liquid distribution device 510, where the fed-back liquid is used as nutrient by the VFA-producing microbes inside TdBR 505, effectively boosting their productivity while at the same time reducing or eliminating the need to externally supply nutrients to TdBR 505.

In a second mode of operation, the "backflush operation mode", feedback module 580 feeds a part of the liquid content of PBR 550 to TdBR's 505 backflush input 510, where the fed-back liquid is used to reverse the flow inside TBR 505. This flow reversal ensures that any nutrient or other coagulations formed on packing material 525 are dissolved and the trickle-down flow of the moisturizing liquid will not be obstructed during nutrient feedback operation mode. Although the design of system's 500 TBR 505 prevents such clogging, clogging may occasionally be formed after very prolonged operation of the system 500. By means of example and without limiting the scope of protection of the present invention, the backflush operation mode may be needed after several hundred or thousand hours of operation and may depend on the type of nutrients fed into TBR 505 and the size and shape of packing material 525.

The backflush operation mode may also be used to expulse packing material outside TdBR 505 (through an opening not shown in FIG. 5) for cleaning or disinfection. Although it not needed to clean or disinfect TdBR 505, this option is available if system 500 is used under different operating conditions and using single or multi-culture microbes under aseptic conditions.

Biomass harvester's 570 output 571, may in other exemplary embodiments be used only for outputting the harvested algae containing liquid of PBR 250, either continuously or in batches, outside of system 500. In such exemplary embodiments, the liquid content of PBR 550 is recirculated into PBR 550, and/or fed back to TdBR 505 from a separate output(s) (not shown in FIG. 5).

The use of feedback module 580 and the nutrient feedback and backflush operation modes, ensure sustainable increased productivity at reduced costs, and uninterrupted operation in non-open systems, respectively.

The operation of feedback module 580, may be implemented using valve(s) 535, 590 connected at each feedback subsystem module 582, 584 pike, either at the respective end connected to output 572 and/or to TdBR's 505 input 590.

Valve 590 is closed when valve 535 opens so that to prevent the liquid (externally to system 500) inputted to TdBR 505 from flowing in reverse flow into feedback module 580, while in backflush operation mode. Similarly, valve 590 opens when valve 535 closes so as to prevent backflushing. The pressure used during backflushing is higher that the pressure used during normal operation.

The orientation and the relative positions of the modules of system 500 may differ from those shown in FIG. 5 without departing from the scope of protection of the present invention. The vertical orientation of TdBR 505 is preferred for optimizing moistening of packing material 525 with a liquid distribution module 510 (e.g. in the form of a single uniform spay-type or rinsing-type design) while maximizing use of the moistening liquid and avoiding flooding part of packing material 525, which would result in TBR 505 productivity drop.

The $CO_2$ fed to $CO_2$ input device 515 may be sourced from any available source. By means of example, it may be "clean" $CO_2$ isolated from offgas or syngas, or other gas mixtures. In another aspect, the $CO_2$ may simply be in a mixture of other gasses (e.g. one including CO), which is supplied from an offgas or syngas source. The presence of other gases together with the $CO_2$ does not cause any problems in the operation of TdBR 405 as the VFA producing microbes are resistant and/or benefitted by the supply of gases other than $CO_2$. This feature of the VFA-producing microbes is used to the benefit of the system's 500 operation of the TdBR 505, by eliminating the need to include a process step to isolate $CO_2$.

In an exemplary embodiment, system 500 operates with $CO_2$ contained in a syngas or offgas mixture, which has been preconditioned. Such a preconditioning step is a standard process used by virtually every producer of such gasses (e.g. industrial installations) due to environmental regulations existing in virtually all countries. Although such regulations differ among countries, and although environmental regulations may change over time, it is highly unlikely, if not impossible, that any such regulations will be abolished in the near future (or at least for the life of the present application and patent) or even relaxed due to the greenhouse effect of $CO_2$ and other gasses and the serious environmental problems they pose by causing global warming. For these reasons, the preconditioning step of syngas and offgas may be considered de facto and not needed to be performed by system 500.

In another aspect, such a preconditioning step may be tuned for producing gas mixtures a certain $CO_2$ concentration. Examples, non-limiting the scope of protection of the present invention, include the following gas mixtures:

45% $H_2$, 20% CO, 25% $CO_2$ vol.
67% $H_2$ and 33% $CO_2$ vol. for full conversion of $CO_2$ and $H_2$ in offgas
a syngas mixture with a Syngas Quality Index (SQI) of 2, where SQI=(% $H_2$+% CO)/(% $CO_2$+% CO) vol.
any composition of up to 20-40% $CO_2$ vol.

During the preconditioning step, hot syngas and/or offgas effectively cools to a much lower temperature (e.g. 5-80° C.) either as the effect of heat loss to the surrounding atmosphere, or as an active cooling process, e.g. with the use of a heat exchanger. Preconditioned gasses at these temperatures can be directly fed to system 500 without further cooling.

In yet another exemplary implementation, only TdBR's 505 $CO_2$ input device 515 has a heat exchange module that cools inputted syngas or offgas at a temperature approximately within the 5-80° C., which is the operating temperature of TdBR 505, dictated by the VFA-producing microbes' tolerance to heat.

In another exemplary implementation, TdBR's 505 CO2 input device 515 does not have a heat exchange module to cool the inputted syngas or offgas at a temperature approximately within the 5-80° C. Such a heat exchange module is not needed as the effluent liquid, fed by feedback module 580 from biomass harvester module 570 to TdBR 405, is already at a lower temperature than the CO2-containing gas (offgas, or syngas, etc.) and together with the existing liquid content of TdBR 505 result in colling the CO2-containing gas. The heat conveyed by the CO2-containing gas to the liquid content of TdBR 505 is dissipated by convection and radiation from TdBR 505, the pipes connecting TdBR 505 to PBR 550, and the pipes recirculating TdBR's 405 liquid content back to TdBR 505. This heat dissipate is enough to allow the temperature inside TdBR 505 to stay relatively stable and in any case within its operating temperature range of 5-80° C.

In an alternative exemplary implementation one or more heat exchange module is added to TdBR 505 or the pipes connecting TdBR 505 with the CO2, H2, nutrient and liquid feedback supplies. Such a heat exchange module may be used either for accurately regulating the operating temperature inside TdBR 505 (e.g. to a preferential narrow operating temperature range for increasing TdBR 505 productivity) or for inputting CO2 gas (or CO2 gas mixtures) to TdBR 505 at temperatures at least 50% higher than the maximum operating temperature of TdBR 505.

In a preferential exemplary implementation, TdBR 505 is operated at approximately 60-80° C. for achieving increased productivity of the VFA-producing microbes.

The VFA containing liquid outputted from TdBR's 505 output 540 is fed directly to PBR's 550 input 555 without cooling it, despite the fact that the micro-algae of PBR 550 can only withstand temperatures of 5-40° C. However, as the flow of VFA-containing liquid into PBR's 550 input 555 is very low compared to the flow of the liquid inside PBR 550, i.e. recirculation of the liquid of PBR 550, resulting in a very low concentration of VFAs in PBR 550 (e.g. 1 lt of VFA-containing liquid per 1000 lt of liquid content of PBR 550), the VFA-containing liquid is very fast cooled to the temperature of the PBR liquid containing the micro-algae and as a result the micro-algae is not killed by the inputted VFA-containing liquid, despite its higher temperature, outside the acceptable range for the micro-algae. An additional advantage of this system design is that there is no need to have a heat exchange module at PBR 550.

It is understood by persons skilled in related art, that system 500 is presented by means of example and that alternative implementations and modes of operation, that are equivalent or have the same or equivalent technical effect fall within the scope of protection of the present invention. It is also assumed that obvious or equivalent modifications, the merging or splitting of modules, as well as, the inclusion of additional but obvious modules and apparatuses (e.g. valves, pumps, cabling, microcontrollers, microprocessors, etc.) not shown in the figures, also fall within the scope of protection of the present invention. These also hold true for the alternative exemplary implementations presented below.

In yet another exemplary embodiment, a stirring module inside PBR 550 stirs the liquid content of the PBR for further enhancing algae productivity by increasing algal exposure to light for enhancing photoautotrophic metabolism.

The design and operation of the fourth embodiment is identical with the second embodiment, except to what concerns the addition of biomass harvester 490.

Packing Material

Figure 6:
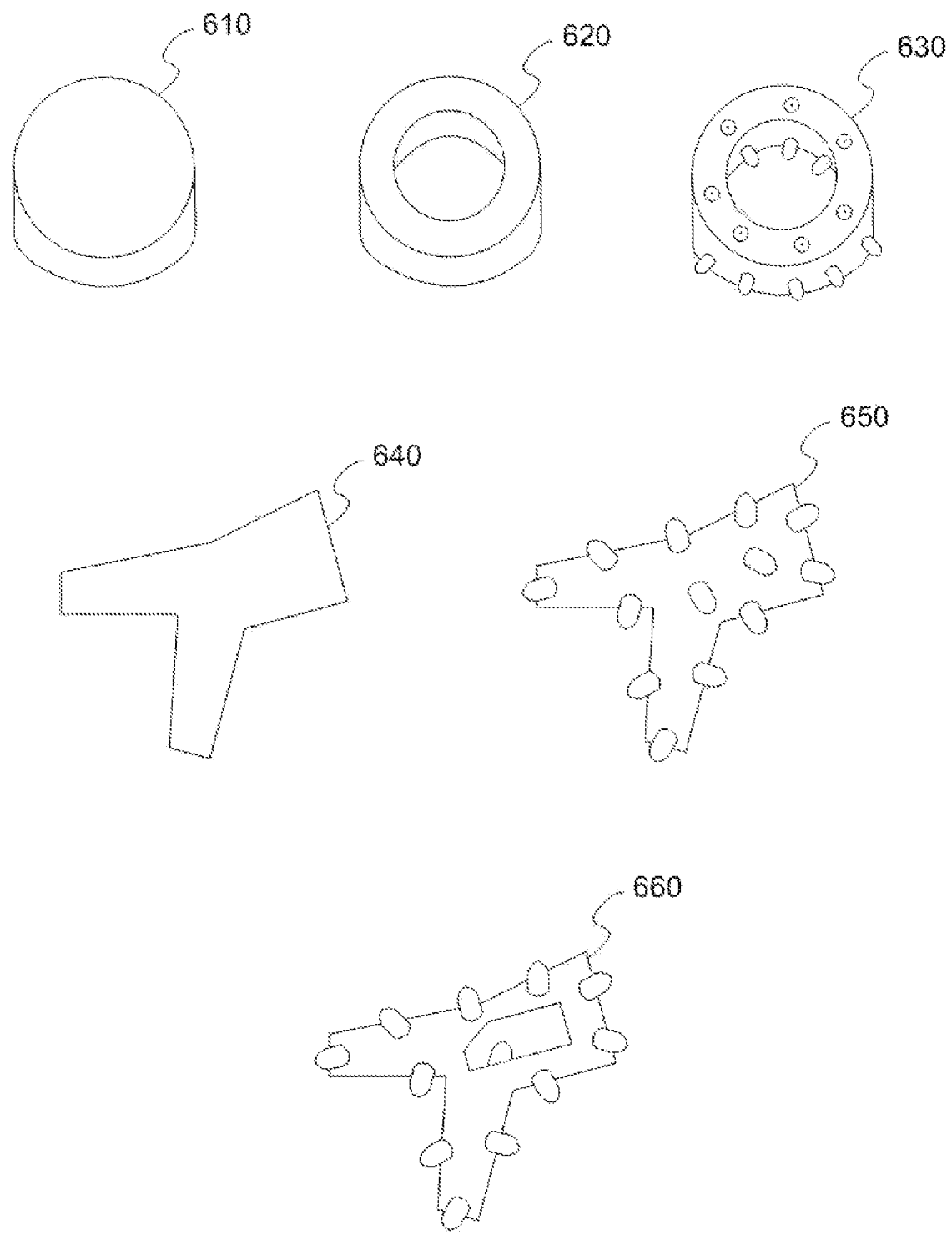
FIG. 6 shows example packing materials used in the TdBR of the present system.

FIG. 6 shows example packing materials used in the TdBR of the present system. The TdBR of the present system contains packing material for increasing the surface for attachment of the VFA-producing microbes for increasing productivity. The packing material is designed, also to minimize clogging that would drop productivity, and the need to regularly clean the packing material, while allowing the packing material to be extracted from the TdBR for sterilization or disinfection, if needed.

In order to fulfill the above requirements, the packing material is constructed from any material that is suitable for use in acidic environments, and which has no pores. Although the presence of micro-pores cannot and does not need to be avoided, materials with surfaces generally accepted as sleek are selected for the packing material. By means of example any known type of synthetic (e.g. plastic, ceramic, etc.) or natural material (e.g. bioplastic, ceramic, etc.) can be used in the construction of the packing material.

The packing material may be formed in particles of virtually any shape that has a surface-to-volume ratio larger than that of a sphere. The higher the ratio, the more suitable the packing material for increasing more the productivity of VFAs in the TdBR. Examples of suitable packing material particles are disks 610 of any height, rings or annuluses or hollow disks 620, rings or annuluses or hollow disks with regular or arbitrary protrusions 630, tri-stars or multi-stars of any profile in any of the three dimensions 640, trihedrons or muli-edron of any profile in any of the three dimensions 650, trihedrons or multihedrons of any profile in any of the three dimensions and with cut-out shapes of any form 650. The 3-Dimensional (3D) shapes of packing material particles shown in FIG. 6 are given only by means of example and should not be interpreted as limiting the scope of protection of the present invention. It is obvious to any person skilled in related art that the shape and the size of the packing material particles can include any shape with a high surface-to-volume ratio (i.e. higher than the surface-to-volume ration of a sphere) and any size that is suitable to fit in the TdBR (i.e. the largest dimension of each packing material particle is smaller than the smallest dimension of the TdBR so as to allow the particle to be unobstructedly positioned in, and removed during backflushing from, the TdBR. Also, the size and shape of the particles can define the amount of packing (i.e. the size of the gaps between the packing material particles after their insertion in the TdBR.

No specific amount of packing is needed for the TdBR to operate. Only a non-perfect packing is needed, i.e. gaps should exist between the packing material particles 225, 325, 425, 525 for the moistening liquid supplied to the packing material by the liquid distribution device 210, 310, 410, 510 to down through the packing material particles and reach output 240, 340, 440, 540.

In an alternative embodiment, the amount of packing of the packing material particles is such that the moistening liquid (which contains nutrients, etc.) just passes unobstructedly through the gaps between the packing material particles, without clogging the packing material particles. Persons skilled in the art can readily appreciate that the amount of packing is determined from the size of the nutrients and other solids in the moistening liquid. So, in order to increase TdBR's productivity by allowing VFA-producing particles to attach to a maximum surface (i.e. that of the packing material used—and also on the inner wall(s) of the TdBR), the packing material may be shaped and dimensioned for the highest packing that still allows the moistening liquid to just trickle down (i.e. pass) unobstructedly through the gaps between the packing material particles, without clogging the packing material particles.

A Methodology for Sustainably Boosting CO2 Fixation for Growing Micro-algae

First Embodiment of the Methodology

Figure 7:
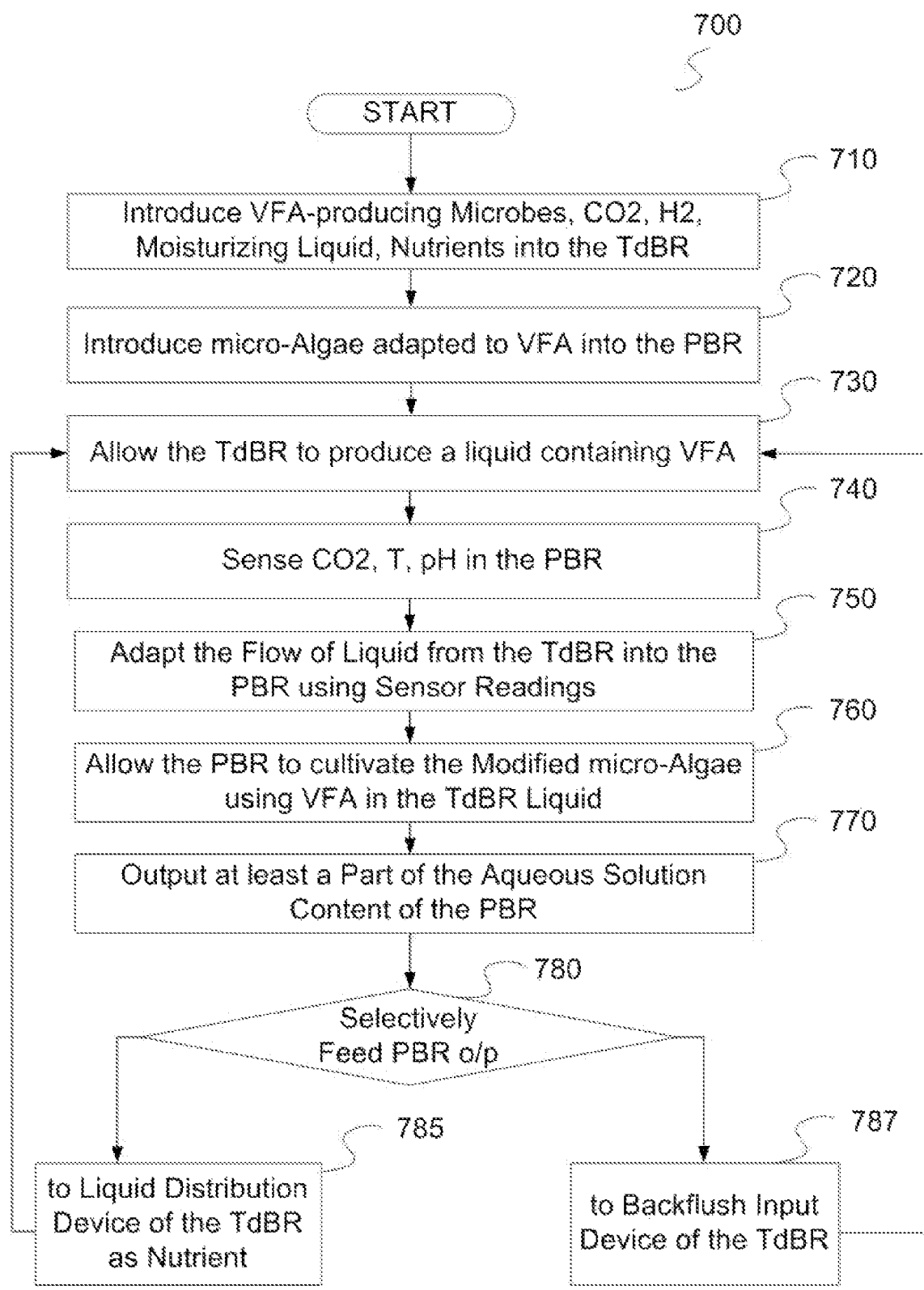
FIG. 7 shows a flow diagram of a first embodiment of a methodology for Sustainably Boosting CO2 Fixation for Growing Micro-algae.

FIG. 7 shows a flow diagram of a first embodiment of a methodology for Sustainably Boosting CO2 Fixation for Growing Micro-algae. Methodology 700 starts by introducing 710 VFA-producing microbes, CO2, H2, moisturizing liquid and nutrients to a TdBR, like the TdBR of FIG. 2-3. Selected or Modified (adapted) micro-algae strains (known from the prior art), suitable for maximum productivity in a liquid containing VFAs, is introduced 720 in a PBR, like the PBR of FIG. 2-3.

Methodology 700 continues by allowing the TdBR (and the VFA-producing microbes) to produce a liquid containing VFAs 730, and continuously (or at intervals) sensing 740 CO2 concentration, and one of more of temperature and pH, in the liquid content of the PBR (which contains VFAs produced by the VFA-producing microbes).

Using the reading(s) of sensing step 740, methodology 700 adapts 750 the flow of a part of the liquid content of the TdBR (which contains VFAs) into the PBR, and allows the TdBR to cultivate 760 the modified micro-algae using the VFAs contained in the liquid content of the TdBR that is supplied to the micro-algae inside the PBR.

Methodology 700 then outputs 770 a part or all of the aqueous solution content of the PBR (which includes micro-algae), and selectively feeds a part or all of the outputted part of the aqueous solution 780 to either a liquid distribution device of the TdBR 785, or to a backflush input device of the TdBR 787. Step 785 is executed when the system (containing the TdBR and PBR of FIG. 2-3) is operating in a "nutrient feedback operation mode" for providing nutrients to TdBR, and step 787 is executed when the system is operating in a "backflush operation mode" for reversing the flow inside the TBR for breaking or dissolving any coagulations formed on the packing material or for expulsing the packing material outside the TdBR for cleaning or disinfection.

During the "nutrient feedback operation mode", the system feeds a part of the aqueous solution content of the PBR into a feedback module, which feeds the aqueous solution to the TdBR's liquid distribution device 210, 310, 410, 510 at a first pressure. The first pressure may take any value that is equal or above the pressure inside the TdBR (which is not operated in flood conditions for ensuring that the liquid distributed into the TdBR by the liquid distribution device 210, 310, 410, 510 always trickles down the packing material without flooding it, as flooding would result in a drop of the productivity of the TdBR). In one aspect the pressure inside the TdBR is 1 Atm.

During the "backflush operation mode", the system feeds a part of the aqueous solution content of the PBR into a feedback module, which feeds the aqueous solution to the TdBR's backflush input 235, 335, 435, 535 at a second pressure. The second pressure may take any value that is above the first pressure and is above the pressure inside the TdBR for reversing flow in the TdBR and effectively ensuring that any nutrient or other solid coagulations formed on the packing material are broken or dissolved and/or the packing material is expulsed from the TdBR for cleaning or disinfection. In one aspect, the second pressure is twice the pressure first pressure.

In one aspect, only one of steps 785 and 787 is executed at any time, so that the system is operated either in the "nutrient feedback operation mode", or in the "backflush operation mode".

In another aspect, both steps 785 and 787 are executed at any time. Since the second pressure is higher than the first pressure, the flow inside the packing material of the TdBR is reversed, as if the system is operated in the "backflush operation mode". This is possible as the packing material is not flooded in the "nutrient feedback operation mode" (i.e. during its normal operation) and there is space for the liquid from the liquid distribution device 210, 310, 410, 510 to continue entering the TdBR. Once the TdBR is flooded, and if more liquid is introduced to the TdBR, the packing material is expulsed from the TdBR, from an expulsion output.

The first embodiment of the methodology is executed on the first or the second embodiments of the system for Sustainably Boosting CO2 Fixation for Growing Micro-algae. In step 710, syngas or offgas or a combination of the two, containing CO2 is input to the TdBR. The syngas or offgas or the combination of the two, includes, for example one of:
  45% H2, 20% CO, 25% CO2 vol.
  67% H2 and 33% CO2 vol. for full conversion of CO2 and H2 in offgas
  a syngas mixture with a Syngas Quality Index (SQI) of 2, where SQI=(% H2+% CO)/(% CO2+% CO) vol.
  any composition of up to 20-40% CO2 vol.

In a modification of the first embodiment of the methodology, an inoculum source is used in step 710 (or in a step prior to step 710) which combines anaerobic sludge from biogas plants with anaerobic sludge from an anaerobic digester fed with manure. The inoculum is prepared by mixing the two anaerobic sludges in equal amounts (50/50 vol./vol.) and adjusting the pH to 6 with 1 Mol HCl while flushing with N2 to ensure anaerobic conditions. This combined inoculum (i.e. the mix) then undergoes a heat-shock treatment to suppress the methanogenic activity of bacteria in the inoculum by heating the mixture of anaerobic sludges up to 90° C. for 15 min while flushing with N2.

The inoculum is further enriched in microbes able to assimilate the gaseous substances by sequential transfers in sealed serum vials as described in GRIMALT-ALEMANY et al., Enrichment of syngas-converting mixed microbial consortia for ethanol production and thermodynamics-based design of enrichment strategies. Biotechnology for Biofuels. Vol. 11, Article No. 198, 19 Jul. 2018. The conditions for the enrichment will be at a gas composition resembling the gas composition of the syngas or offgas or the combination of the two and at a pH of 5-7.

By means of example and without liming the scope of protection of the present innovative solution, an indicative productivity of 15 g acetate/L bed/day is achieved by the TdBR, which may be increased or decreased in modifications of size of the TdBR used in the system. VFAs include modular ratio of acetate, propionate, butyrate and valerate. No isolation of acetate or other VFAs is needed. No concentration of the VFA containing liquid output of the TdBR is required, and a liquid with a content of approximately 1%-100% vol. may be fed to the PBR without harming the micro-algae, for the reasons presented above.

In one aspect the TdBR is operated at 0.1-2 hour Empty Bed Residence Time (EBRT) for the gas and a pH between 4.5-7.5.

The PBR is operated in mixotrophic conditions with the following parameters:

4,5-9,5 pH
10° C.-40° C.
pressure of 1 Atm.
operation even in the absence of CO2 or O2 injection
light sources can be selected among sunlight, Light-Emitting Diodes (LED), fluorescent tube, incandescent bulbs, neon lights with a light intensity, for example, in the range of 3000-10000 KLumens or less.
exemplary air flow (containing O2) is approximately 60 L/min; other rates can be used below or above this example
exemplary air pressure is approximately 0.15 bar; other rates can be used below or above this example
exemplary liquid velocity is 0.2 m/s; other velocities can be used below or above this example
exemplary quantity of VFA added to PBR per litre of liquid inside the PBR is 15-20 gr/lt; other quantities can be used below or above this example In one aspect biomass-harvester module 470 is first dewatered through centrifugation, then dried through freeze-drying, then the cell is disrupted through bead milling, and finally two phases (hydrophobic and hydrophilic) are obtained through solvent extraction.

In order to allow efficient backflushing and packing material expulsion from the TdBR for cleaning/disinfection, the packing material is chosen so as to float when flooded or soaked in the liquid inside the TdBR. By means of example and without limiting the scope of protection of the present innovative solution, the packing material has a surface area of 800 m2/m3 and density 1 g/cm3.

Second Embodiment of the Methodology

Figure 8:
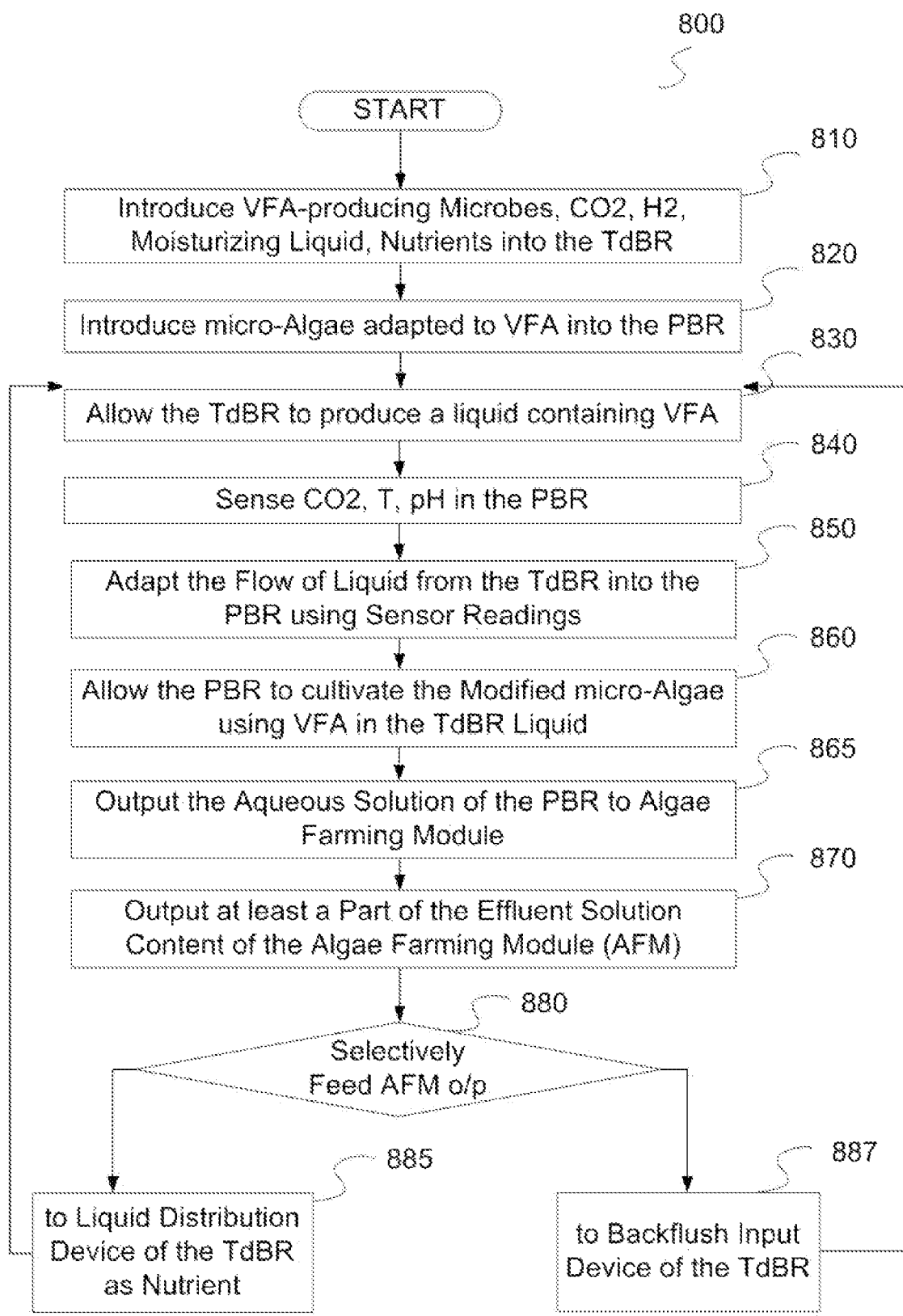
FIG. 8 shows a flow diagram of a second embodiment of a methodology for Sustainably Boosting CO2 Fixation for Growing Micro-algae.

FIG. 8 shows a flow diagram of a second embodiment of a methodology for Sustainably Boosting CO2 Fixation for Growing Micro-algae. Methodology 800 starts by introducing 810 VFA-producing microbes, CO2, H2, moisturizing liquid and nutrients to a TdBR, like the TdBR of FIG. 4-5. Modified algae, suitable for maximum productivity in a liquid containing VFAs, is introduced 820 in a PBR, like the PBR of FIG. 4-5.

Methodology 800 continues by allowing the TdBR (and the VFA-producing microbes) to produce a liquid containing VFAs 830, and continuously (or at intervals) sensing 840 CO2 concentration, and one of more of temperature and pH, in the liquid content of the PBR (which contains VFAs produced by the VFA-producing microbes).

Using the reading(s) of sensing step 840, methodology 800 adapts 850 the flow of a part of the liquid content of the TdBR (which contains VFAs) into the PBR, and allows the TdBR to cultivate 860 the modified micro-algae using the VFAs contained in the liquid content of the TdBR that is supplied to the micro-algae inside the PBR.

Methodology 800 then outputs 865 the aqueous solution content of the PBR (which includes micro-algae) to an algae farming module which extracts part or all the algae contained in the aqueous solution fed to the algae farming module. The extracted algae may then be used externally to the system of FIG. 8 as is or as a first material for other mechanical, biological, or chemical process(es) leaving an effluent liquid which may still contain algae.

Methodology 800 then outputs 870 a part or all of the effluent solution content of the algae farming module (which may still include micro-algae), and selectively feeds a part or all of the outputted part of the aqueous solution 880 to either a liquid distribution device of the TdBR 885, or to a backflush input device of the TdBR 887. Step 885 is executed when the system (containing the TdBR and PBR of FIG. 4-5) is operating in a "nutrient feedback operation mode" for providing nutrients to TdBR, and step 887 is executed when the system is operating in a "backflush operation mode" for reversing the flow inside the TBR for breaking or dissolving any coagulations formed on the packing material or for expulsing the packing material outside the TdBR for cleaning or disinfection.

During the "nutrient feedback operation mode", the system feeds a part of the aqueous solution content of the algae farming module into a feedback module, which feeds the aqueous solution to the TdBR's liquid distribution device 210, 310, 410, 510 at a first pressure. The first pressure may take any value that is just above the pressure inside the TdBR (which is not operated in fluid conditions for ensuring that the liquid distributed into the TdBR by the liquid distribution device 210, 310, 410, 510 always trickles down the packing material without flooding it, as flooding would result in a drop of the productivity of the TdBR).

During the "backflush operation mode", the system feeds a part of the aqueous solution content of the algae farming module into a feedback module, which feeds the aqueous solution to the TdBR's backflush input 235, 335, 435, 535 at a second pressure. The second pressure may take any value that is above the first pressure and is above the pressure inside the TdBR for reversing flow in the TdBR and effectively ensuring that any nutrient or other solid coagulations formed on the packing material are broken or dissolved and/or the packing material is expulsed from the TdBR for cleaning or disinfection.

In one aspect, only one of steps 885 and 887 is executed at any time, so that the system is operated either in the "nutrient feedback operation mode", or in the "backflush operation mode".

In another aspect, both steps 885 and 887 are executed at any time. Since the second pressure is higher than the first pressure, the flow inside the packing material of the TdBR is reversed, as if the system is operated in the "backflush operation mode". This is possible as the packing material is not flooded in the "nutrient feedback operation mode" (i.e. during its normal operation) and there is space for the liquid from the liquid distribution device 210, 310, 410, 510 to continue entering the TdBR. Once the TdBR is flooded, and if more liquid is introduced to the TdBR, the packing material is expulsed from the TdBR, from the expulsion output.

The Second embodiment of the methodology is executed on the third or the fourth embodiment of the system for Sustainably Boosting CO2 Fixation for Growing Micro-algae. In step 810, syngas or offgas or a combination of the two, containing CO2 is input to the TdBR. The syngas or offgas or the combination of the two, includes, for example one of:
  45% H2, 20% CO, 25% CO2 vol.
  67% H2 and 33% CO2 vol. for full conversion of CO2 and H2 in offgas
  a syngas mixture with a Syngas Quality Index (SQI) of 2, where SQI=(% H2+% CO)/(% CO2+% CO) vol.
  any composition of up to 20-40% CO2 vol.

In a modification of the second embodiment of the methodology, an inoculum source is used in step 810 (or in a step prior to step 810) which combines anaerobic sludge from biogas plants with anaerobic sludge from an anaerobic digester fed with manure. The inoculum is prepared by mixing the two anaerobic sludges in equal amounts (50/50 vol./vol.) and adjusting the pH to 6 with 1 Mol HCl while flushing with N2 to ensure anaerobic conditions. This combined inoculum (i.e. the mix) then undergoes a heat-shock treatment to suppress the methanogenic activity of bacteria in the innoculum by heating the mixture of anaerobic sludges up to 90° C. for 15 min while flushing with N2.

The inoculum is further enriched in microbes able to assimilate the gaseous substances by sequential transfers in sealed serum vials as described in GRIMALT-ALEMANY et al., Enrichment of syngas-converting mixed microbial consortia for ethanol production and thermodynamics-based design of enrichment strategies. Biotechnology for Biofuels. Vol. 11, Article No. 198, 19 Jul. 2018. The conditions for the enrichment will be at a gas composition resembling the gas composition of the syngas or offgas or the combination of the two and at a pH of 5-7.

Software Architecture

Figure 9:
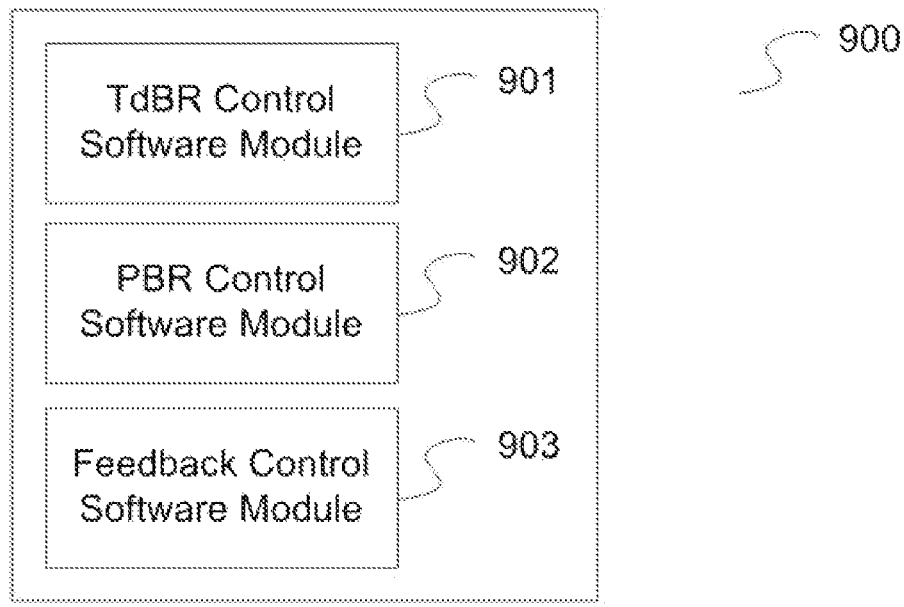
FIG. 9 shows a schematic diagram of software architecture 900 that is run by the electronics hardware of the system.

The system of FIGS. 2-5 and the methodology of FIGS. 6-7 may be controlled manually (e.g. via analogue sensors whose readings are read by a human operator, who then manually adjusts the operation of pumps valves, etc.) or automatically by a control system that is implemented in general-purpose electronics hardware (i.e. general purpose computer(s), microprocessor(s) and electronics, which run software or firmware, that transform them into hardware adapted to implementing the present system and methodology, or is implemented in purpose-built electronics hardware (e.g. Application Specific Integrated Circuits (ASIC) etc.) that are hard-wired to implemented exclusively the present system and methodology FIG. 9 shows a schematic diagram of software architecture 900 that is run by the electronics hardware of the system. Software architecture 900 may be written in any programming language, or as embedded software, or firmware, that has, in an exemplary implementation, the following software modules:

TdBR control software module 901, which controls all the parameters of the TdBR module's operation by controlling pumps, valves, etc. of the TdBR module PBR control software module 902, which controls all the parameters of the PBR module's operation by controlling pumps, valves, etc. of the PBR module Feedback control software module 903, which controls all the parameters of the feedback module's operation by controlling pumps, valves, etc. of the feedback module It is obvious to persons skilled in the art that other software modules may be added or the above modules may be merged, or split without departing from the scope of the protection of the present invention.

The present innovative solution can also be implemented by software written in any programming language, or in an abstract language (e.g. a metadata-based description which is then interpreted by a software or hardware component). The software running in the above-mentioned hardware, effectively transforms a general-purpose or a special-purpose hardware or computing device, apparatus or system into one that specifically implements the present innovative solution. In another aspect an embedded system is used for the wearable device.

Hardware Architecture

Figure 10:
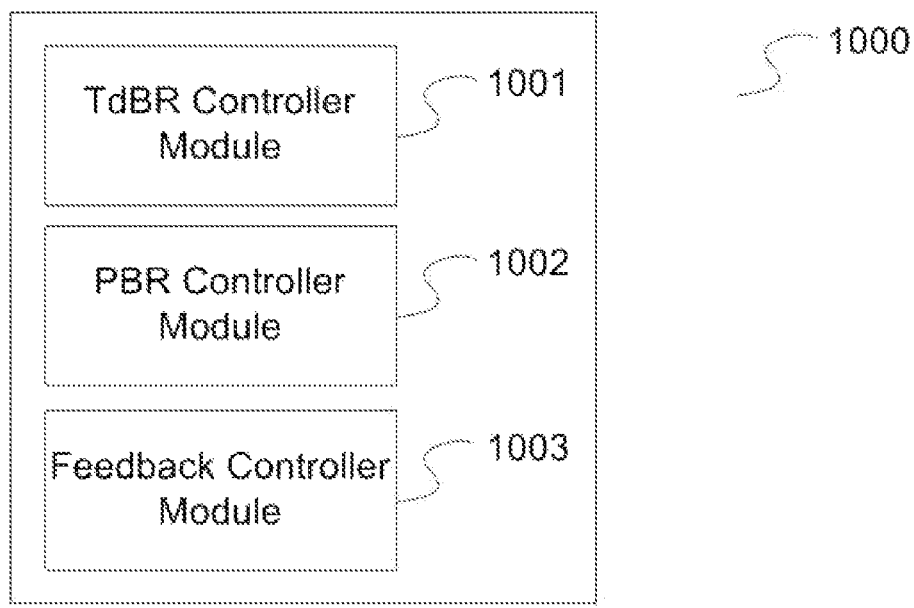
FIG. 10 shows a schematic diagram of the electronics hardware architecture of the system.

FIG. 10 shows a schematic diagram of the electronics hardware architecture of the system. Electronics hardware architecture 1000 has, in an exemplary implementation, the following electronics hardware modules:

TdBR controller module 1001, which controls all the parameters of the TdBR module's operation by controlling pumps, valves, etc. of the TdBR module PBR controller module 1002, which controls all the parameters of the PBR module's operation by controlling pumps, valves, etc. of the PBR module Feedback controller module 1003, which controls all the parameters of the feedback module's operation by controlling pumps, valves, etc. of the feedback module In a modified exemplary implementation, the photo-bioreactor is replaced by a bioreactor which can operate both in the presence and absence of light. This choice is made possible by using micro-algae that does not rely on light as an energy source (e.g. Chlorella or other known micro-algae that can grow without light); instead, the photo-bioreactor uses VFAs as energy to cultivate micro-algae.

In another exemplary implementation the system may use both a bioreactor and a photo-bioreactor.

In the previous and the following parts, the term "microalgae cultivation module" is used to mean any of "photo-bioreactor", "PBR", "bioreactor", and "photo-bioreactor and bioreactor" unless it is obvious that only one is meant.

It is obvious to persons skilled in the art that other electronics hardware modules may be added or the above modules may be merged, or split without departing from the scope of the protection of the present invention.

The sensing and the adjusting steps and the corresponding modules of the present innovative solution can be implemented in Application Specific Integrated Circuits (ASIC) or other hardware technology.

The above exemplary embodiment descriptions are simplified and do not include hardware (mechanical, electrical or electronic) and software elements that are used in the embodiments but are not part of the current invention, are not needed for the understanding of the embodiments, and are obvious to any user of ordinary skill in related art. Furthermore, variations of the described system architecture are possible, where, for instance, some servers may be omitted or others added.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventor that the words and phrases in the specification and claims be given the ordinary and accustomed meanings to those of ordinary skill in the applicable art(s).

The foregoing description of a preferred embodiment and best mode of the invention known to the applicant at this time of filing the application has been presented and is intended for the purposes of illustration and description. It is not intended to be exhaustive or limit the invention to the precise form disclosed and many modifications and variations are possible in the light of the above teachings. The embodiment was chosen and described in order to best explain the principles of the invention and its practical application and to enable others skilled in the art to best utilize the invention in various embodiments and with various modifications as are suited to the particular use contemplated. Therefore, it is intended that the invention not be limited to the particular embodiments disclosed for carrying out this invention, but that the invention will include all embodiments falling within the scope of the appended claims.

In one or more exemplary embodiments, the functions described may be implemented in hardware, software, firmware, or any combination thereof. If implemented in software, the functions may be stored on or transmitted over as one or more instructions or code on a computer readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. Disk and disc, as used herein, includes compact disc (CD), laser disc, optical disc, digital versatile disc (DVD), floppy disk and blu-ray disc where disks usually reproduce data magnetically, while discs reproduce data optically with lasers. Combinations of the above should also be included within the scope of computer-readable media.

The previous description of the disclosed exemplary embodiments is provided to enable any person skilled in the art to make or use the present invention. Various modifications to these exemplary embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A system for sustainably boosting CO2 fixation into organic acids and using the organic acids for boosting the growing of micro-algae, comprising:
   a Trickle Bed Reactor (TBR), configured as at least one plug flow pro-current reactor for growing Volatile Fatty Acids (VFA)-producing microbes, wherein the TBR comprises (a) a non-porous packing material configured as floatable particles of high surface-to-volume ratio which when packed form gaps between the particles for allowing a moistening liquid to pass, suitable for use in acidic environments, and for moistening with the moistening liquid, (b) a liquid distribution device connected at an input at a first upper point of the TBR and configured for introducing into the TBR at least one of nutrients, VFA-producing microbes, and the moistening liquid, (c) a CO2 input device connected at a second upper point of the TBR and configured for introducing CO2 into the TBR from a CO2 source external to the system; (d) a H2 input device connected at a third upper point of the TBR and configured for introducing H2 into the TBR from an H2 source external to the system, (e) a backflush input device connected at a first bottom point of the TBR and configured for at least one of unclogging and cleaning the packing material by reversing flow in the TBR, and (f) an output connected at a first bottom point of the TBR and configured for outputting a liquid comprising VFA;
   a microalgae cultivation module for pro-current mixotrophic micro-algae cultivation, wherein the microalgae uses VFA as a carbon source, the microalgae cultivation module comprising (g) an input at an upper point of the microalgae cultivation module and connected to the output of the TBR, the microalgae cultivation module being configured as at least one tube-like structure, (h) a sensory module configured for detecting at least one of a concentration of CO2, temperature, and pH in the microalgae cultivation module, and for adjusting the flow into the microalgae cultivation module of the liquid comprising VFA to at least one of the concentration of CO2, temperature, and pH in the microalgae cultivation module, and (j) an output at a bottom point of the microalgae cultivation module configured for outputting a first aqueous solution comprising micro-algae;
   a biomass harvester comprising an input connected to the output of the microalgae cultivation module, and an output, wherein the output is configured for outputting a second aqueous solution that remains after the algae has been harvested from the first aqueous solution;
   a feedback module connected to the output of the biomass harvester via a first valve, wherein (k) the first valve is also connected to a second valve and to the liquid distribution device, and (l) the second valve is also connected to an output of the system and to a backflush input connected to a second bottom point of the TBR; and
   at least one controller module connected to at least the first and the second valve, wherein the at least one controller module is configured for one of (m) controlling the second valve to feed at least part of the second aqueous solution from the output of the system to the liquid distribution device, and the first valve to feed all the second aqueous solution from the output of the biomass harvester to the second valve, and (n) controlling the second valve to stop feeding the second aqueous solution to any of the output of the system and the liquid distribution device, and the first valve to feed all the second aqueous solution from the output of the biomass harvester to the backflush input.

2. The system of claim 1, further comprising an inoculum source connected to the CO2 input device and configured for enriching syngas containing CO2.

3. The system of claim 1, wherein the packing material is formed into particles having a surface area of 800 m2/m3 and density 1 g/cm3.

4. The system of claim 1, wherein the packing material is formed into particles shaped as one of disks, rings, annuluses, hollow disks, rings with protrusions, annuluses with protrusions, hollow disks with protrusions, tri-stars, multi-stars, trihedrons, muli-edrons, trihedrons with cut-out shapes, multihedrons with cut-out shapes.

5. A method for sustainably boosting CO2 fixation into organic acids and using the organic acids for boosting the growing of micro-algae, comprising:
   introducing Volatile Fatty Acid (VFA)-producing microbes, CO2, H2 and nutrients into a Trickle Bed Reactor (TBR) of a system according to claim 1;
   introducing micro-algae, configured for using Volatile Fatty Acids (VFA) as a carbon source, into a microalgae cultivation module;
   allowing the TBR to operate pro-current and produce a liquid comprising VFA;
   sensing with a sensory module at least one of a concentration of CO2, temperature, and pH in the microalgae cultivation module and feeding the liquid comprising VFA to the microalgae cultivation module, by first adjusting the flow of the liquid comprising VFA into the microalgae cultivation module to the concentration of at least one of CO2, temperature, and pH in the microalgae cultivation module;

allowing the microalgae cultivation module to operate pro-current and cultivate micro-algae using the VFA in the liquid containing VFA as a carbon source, and outputting a first aqueous solution containing micro-algae to a biomass harvester;

harvesting with the biomass harvester the micro-algae from the first aqueous solution containing micro-algae;

outputting from the biomass harvester to a feedback module a second aqueous solution that remains after the algae has been harvested from the first aqueous solution;

controlling the feedback module to selectively feed, using a first valve connected to a second valve and to a liquid distribution device connected to an input of the TBR, the output of the biomass harvester to one of (i) a backflush input device connected at a first bottom point of the TBR, for one of unclogging, cleaning and disinfecting a packing material inside the TBR, by reversing flow in the TBR at a second pressure value by connecting with the first valve the output of the biomass harvester to the backflush input device while isolating the first valve from the second valve, and (ii) a liquid distribution device connected at an input at a first upper point of the TBR by isolating the first valve from the backflush input device, connecting the first valve with the second valve and selectively feeding at least a part of the aqueous solution from the output of the biomass harvester to the liquid distribution device of the TBR as nutrient at a first pressure value, wherein the second pressure value is higher than the first pressure value;

wherein the packing material is configured as floatable particles of high surface-to-volume ratio, suitable for use in acidic environments, and for moistening with a moistening liquid.

6. The method of claim 5, wherein the VFA-producing microbes in the TBR are selected from a set containing a single species of VFA-producing microbes, a culture of two or more species of VFA-producing microbes, and a culture of VFA-producing microbes and other microbe species, and the micro-algae is at least one of selected, adapted and modified to acidic conditions.

7. The method of claim 5, further comprising recirculating the liquid content of the microalgae cultivation module into the microalgae cultivation module by feeding the liquid content of the microalgae cultivation module from the microalgae cultivation module output back to the microalgae cultivation module for further enhancing micro-algae productivity.

8. The method of claim 5, wherein the CO2 introduced into the TBR is comprised in one of a syngas, an offgas and a mixture of syngas and offgas having a gas concentration of one of:
   45% H2, 20% CO, 25% CO2 vol.;
   67% H2 and 33% CO2 vol. for full conversion of CO2 and H2 in offgas;
   a syngas mixture with a Syngas Quality Index (SQI) of 2, where SQI=(% H2+% CO)/(% CO2+% CO) vol.; and
   up to 20-40% CO2 vol.

9. The method of claim 8, wherein the CO2 introduced into the TBR is at a temperature approximately within the 5-80° C.

10. The method of claim 8, wherein the TBR is operated at approximately 60-80° C.

11. The method of claim 5, further comprising an inoculum source used in the step of introducing Volatile Fatty Acid (VFA)-producing microbes, CO2, H2 and nutrients into the TBR), where the inoculum source:
   combines anaerobic sludge from biogas plants with anaerobic sludge from an anaerobic digester fed with manure;
   is prepared by mixing the anaerobic sludge from biogas plants and the anaerobic sludge from an anaerobic digester fed with manure in equal amounts (50/50 vol./vol.) and adjusting the pH to 6 with 1 Mol HCl while flushing with N2 to ensure anaerobic conditions; and
   the mix then undergoes a heat-shock treatment to suppress the methanogenic activity of bacteria in the inoculum by heating the mix of anaerobic sludges up to 90° C. for 15 min while flushing with N2.

12. The method of claim 11, further comprising the inoculum being further enriched in microbes able to assimilate gases in the one of the syngas, the offgas and the mixture of syngas and offgas by sequential transfers in sealed serum vials, wherein the conditions for the enriching are at a gas concentration resembling the gas concentration of the one of the syngas, the offgas and the mixture of syngas and offgas and at a pH of 5-7.

* * * * *